(12) United States Patent
Kim et al.

(10) Patent No.: US 12,329,403 B2
(45) Date of Patent: Jun. 17, 2025

(54) END EFFECTOR AND END EFFECTOR DRIVE APPARATUS

(71) Applicants: BOARD OF REGENTS OF THE UNIVERSITY OF TEXAS SYSTEM, Austin, TX (US); Endoquest Robotics, Inc., Houston, TX (US)

(72) Inventors: Daniel H. Kim, Houston, TX (US); Dong Suk Shin, Houston, TX (US); Taeho Jang, Houston, TX (US); Yongman Park, Houston, TX (US); Jeihan Lee, Houston, TX (US); Hongmin Kim, Houston, TX (US); Kihoon Nam, Gwangmyeong (KR); Seokyung Han, Houston, TX (US)

(73) Assignees: BOARD OF REGENTS OF THE UNIVERSITY OF TEXAS SYSTEM, Austin, TX (US); Endoquest Robotics, Inc., Houston, TX (US)

( * ) Notice: Subject to any disclaimer, the term of this patent is extended or adjusted under 35 U.S.C. 154(b) by 0 days.

(21) Appl. No.: 18/510,452

(22) Filed: Nov. 15, 2023

(65) Prior Publication Data
US 2024/0081849 A1    Mar. 14, 2024

Related U.S. Application Data

(62) Division of application No. 17/013,311, filed on Sep. 4, 2020, now Pat. No. 12,011,188, which is a division (Continued)

(51) Int. Cl.
*A61B 17/29* (2006.01)
*A61B 34/00* (2016.01)
(Continued)

(52) U.S. Cl.
CPC .............. *A61B 17/29* (2013.01); *A61B 34/71* (2016.02); *A61B 90/30* (2016.02); (Continued)

(58) Field of Classification Search
CPC ......... A61B 17/29; A61B 34/71; A61B 90/30; A61B 2017/0034; A61B 2017/00477; (Continued)

(56) References Cited

U.S. PATENT DOCUMENTS 4,919,112 A * 4/1990 Siegmund ............ A61B 1/0052
                                                   600/146
5,810,876 A   9/1998 Kelleher
(Continued)

FOREIGN PATENT DOCUMENTS

CN    101616636 A    12/2009
CN    101530340 B    8/2013
(Continued)

OTHER PUBLICATIONS

PCT International Search Report and Written Opinion for Application No. PCT/US2018/066828, Dated Apr. 17, 2019.
(Continued)

*Primary Examiner* — T. Scott Fix
(74) *Attorney, Agent, or Firm* — Patterson + Sheridan, LLP

(57) ABSTRACT

Provided herein is a mechanism to controllably move a wire within a flexible tubular member, the wire including opposed wire ends extending outwardly of a proximal end of the flexible tubular member, comprising a drive mechanism and a coupling located between the drive mechanism and the wire end, wherein movement of the coupling in the direction of the wire end results in opposed motion of the wire end.

6 Claims, 20 Drawing Sheets

Related U.S. Application Data of application No. 16/495,038, filed as application No. PCT/US2018/066828 on Dec. 20, 2018, now Pat. No. 10,881,422.

(60) Provisional application No. 62/612,220, filed on Dec. 29, 2017.

(51) Int. Cl.
*A61B 90/30* (2016.01)
*A61B 17/00* (2006.01)
*A61B 17/34* (2006.01)

(52) U.S. Cl.
CPC ............... *A61B 2017/0034* (2013.01); *A61B 2017/00477* (2013.01); *A61B 2017/2905* (2013.01); *A61B 2017/2906* (2013.01); *A61B 2017/2939* (2013.01); *A61B 2017/3445* (2013.01)

(58) Field of Classification Search
CPC .... A61B 2017/2905; A61B 2017/2906; A61B 2017/2939; A61B 2017/3445
USPC .......... 74/469, 479.01, 490.04; 446/361, 362, 446/363, 425
See application file for complete search history.

(56) References Cited

U.S. PATENT DOCUMENTS

| | | | |
|---|---|---|---|
| 6,394,998 | B1 | 5/2002 | Wallace et al. |
| 6,568,869 | B1 * | 5/2003 | Murata ................ B62D 57/02 446/129 |
| 6,818,007 | B1 | 11/2004 | Dampney et al. |
| 6,840,938 | B1 | 1/2005 | Morley et al. |
| 7,574,250 | B2 | 8/2009 | Niemeyer |
| 7,744,608 | B2 | 6/2010 | Lee et al. |
| 8,123,740 | B2 | 2/2012 | Madhani et al. |
| 8,337,521 | B2 | 12/2012 | Cooper et al. |
| 8,888,764 | B2 | 11/2014 | Devengenzo et al. |
| 9,295,522 | B2 | 3/2016 | Kostrzewski |
| 9,492,233 | B2 | 11/2016 | Williams |
| 9,775,678 | B2 * | 10/2017 | Lohmeier .............. A61B 34/76 |
| 9,844,389 | B2 | 12/2017 | Van Andel |
| 2005/0222495 | A1 | 10/2005 | Okada et al. |
| 2007/0156019 | A1 | 7/2007 | Larkin et al. |
| 2008/0119870 | A1 | 5/2008 | Williams |
| 2010/0016853 | A1 | 1/2010 | Burbank |
| 2010/0318101 | A1 | 12/2010 | Choi |
| 2011/0196419 | A1 | 8/2011 | Cooper |
| 2011/0238064 | A1 | 9/2011 | Williams |
| 2011/0277580 | A1 | 11/2011 | Cooper et al. |
| 2012/0296341 | A1 | 11/2012 | Seibold et al. |
| 2014/0338477 | A1 | 11/2014 | Donlon et al. |
| 2014/0358162 | A1 | 12/2014 | Valdastri et al. |
| 2015/0051619 | A1 | 2/2015 | Cooper et al. |
| 2015/0127019 | A1 | 5/2015 | Komuro et al. |
| 2015/0150634 | A1 | 6/2015 | Isoda |
| 2017/0071458 | A1 | 3/2017 | Yanagihara et al. |
| 2017/0095139 | A1 | 4/2017 | Yanagihara et al. |
| 2017/0097035 | A1 | 4/2017 | Zimmerman et al. |
| 2017/0119418 | A1 | 5/2017 | Yoshimura |
| 2017/0231653 | A1 | 8/2017 | Kapadia |

FOREIGN PATENT DOCUMENTS

| | | |
|---|---|---|
| CN | 105025826 A | 11/2015 |
| CN | 104582627 B | 7/2017 |
| CN | 107361820 A | 11/2017 |
| CN | 107405172 A | 11/2017 |
| DE | 102013005493 A1 | 10/2014 |
| JP | 2010069003 A | 4/2010 |
| JP | 2010512852 A | 4/2010 |
| JP | 2013215506 A | 10/2013 |
| JP | 2015535702 A | 12/2015 |
| JP | 2016039918 A | 3/2016 |
| JP | 2017018465 A | 1/2017 |
| WO | 2008070556 A1 | 6/2008 |
| WO | 2010039394 A1 | 4/2010 |
| WO | 2013/077571 A1 | 5/2013 |
| WO | 2013184477 A2 | 12/2013 |
| WO | 2014046618 A1 | 3/2014 |
| WO | 2015151093 A1 | 10/2015 |
| WO | 2016075241 A1 | 5/2016 |
| WO | 2017064305 A1 | 4/2017 |
| WO | 2017136710 A | 8/2017 |

OTHER PUBLICATIONS

Taiwan Patent Application No. 107146561, Office Action dated Aug. 7, 2019, 13 pages.
Australian Patent No. 2018394076, Examination Report No. 1 dated Dec. 13, 2019, 5 pages.
Australian Patent No. 2018394076, Examination Report No. 2 dated Apr. 9, 2020, 4 pages.
Canadian Patent Application No. 3,063,459, Office Action dated May 11, 2020, 4 pages.
Australian Examination Report dated Aug. 14, 2020, for Australian Patent Application No. 2020202418.
Australian Application No. 2020210173, Examination Report No. 1 dated Oct. 28, 2020, 5 pages.
Australian Examination Report dated Mar. 5, 2021, for Australian Patent Application No. 2020202418.
Taiwan Patent Application No. 108148267, Office Action dated Apr. 19, 2021, 27 pages.
Korean Patent Application No. 10-2020-7020970, Office Action dated Jun. 23, 2021, 12 pages.
Korean Patent Application No. 10-2020-7020966, Office Action dated Jun. 22, 2021 w/Engilsh Translation, 10 pages.
European Patent Application No. 18897369.7, Supplementary Partial European Search Report dated Aug. 13, 2021, 10 pages.
Japanese Office Action dated Sep. 28, 2021, for Japanese Patent Application No. 2020-160044.
Japanese Office Action dated Oct. 5, 2021, for Japanese Patent Application No. 2020-160039.
Canadian Office Action dated Oct. 8, 2021, for Canadian Patent Application No. 3,091,734.
Canadian Office Action dated Oct. 18, 2021, for Canadian Patent Application No. 3,091,728.
EPO Supplementary European Search Report dated Nov. 25, 2021, for European Application No. 18897369.7.
Korean Office Action dated Dec. 21, 2121, for Korean Patent Application No. 10-2020-7020970.
Japanese Decision to Grant a Patent dated Jan. 11, 2022, for Japanese Patent Application No. 2020-160044.
Taiwan Office Action dated Feb. 11, 2022, for Taiwan Patent Application No. 109115754.
Canadian Office Action dated Apr. 20, 2022, for Canadian Patent Application No. 3,148,897.
Chinese Patent Application No. 201880034397.2, Office Action dated May 16, 2022 w/English translation, 18 pages.
Chinese Office Action dated May 16, 2022, for Chinese Patent Application No. 201880034397.2.
Japanese Notice of Allowance dated May 31, 2022, for Japanese Patent Application No. 2020-160039.
Canadian Office Action dated Jul. 5, 2022, for Canadian Patent Application No. 3,091,728.
Taiwan Office Action dated Oct. 25, 2022, for Taiwan Patent Application No. 109115754.
Canadian Office Action dated Feb. 22, 2023, for Canadian Patent Application No. 3,091,728.
Extended European Search Report dated Nov. 21, 2023, for European Application No. 23201732.7.
Extended European Search Report dated Nov. 23, 2023, for European Application No. 23201728.5.

* cited by examiner

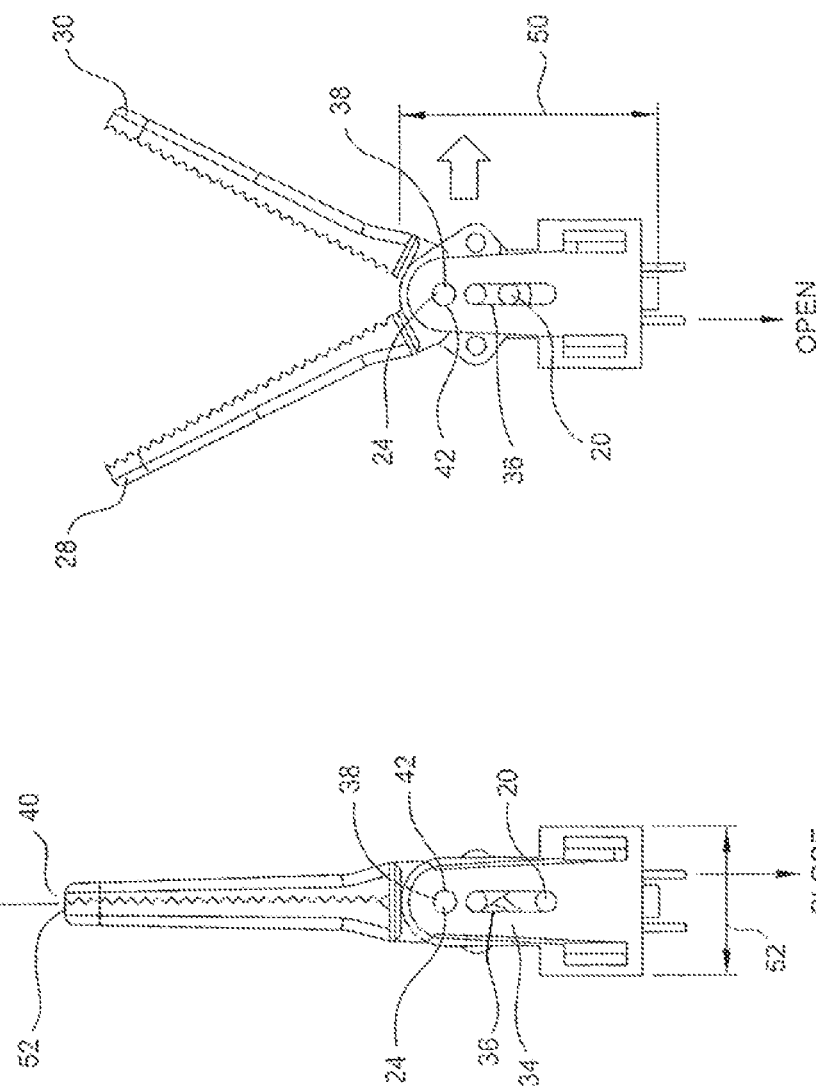

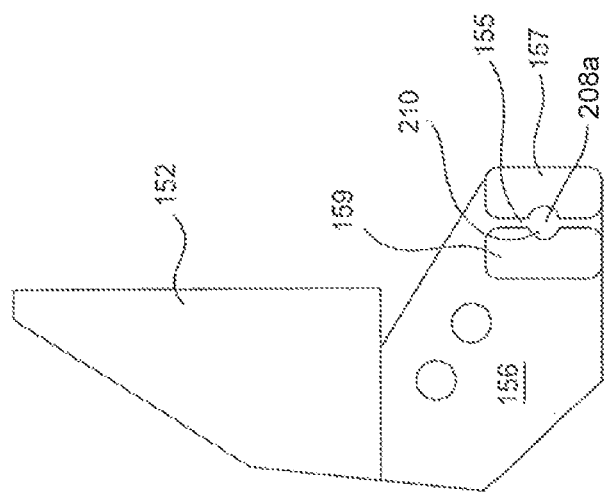

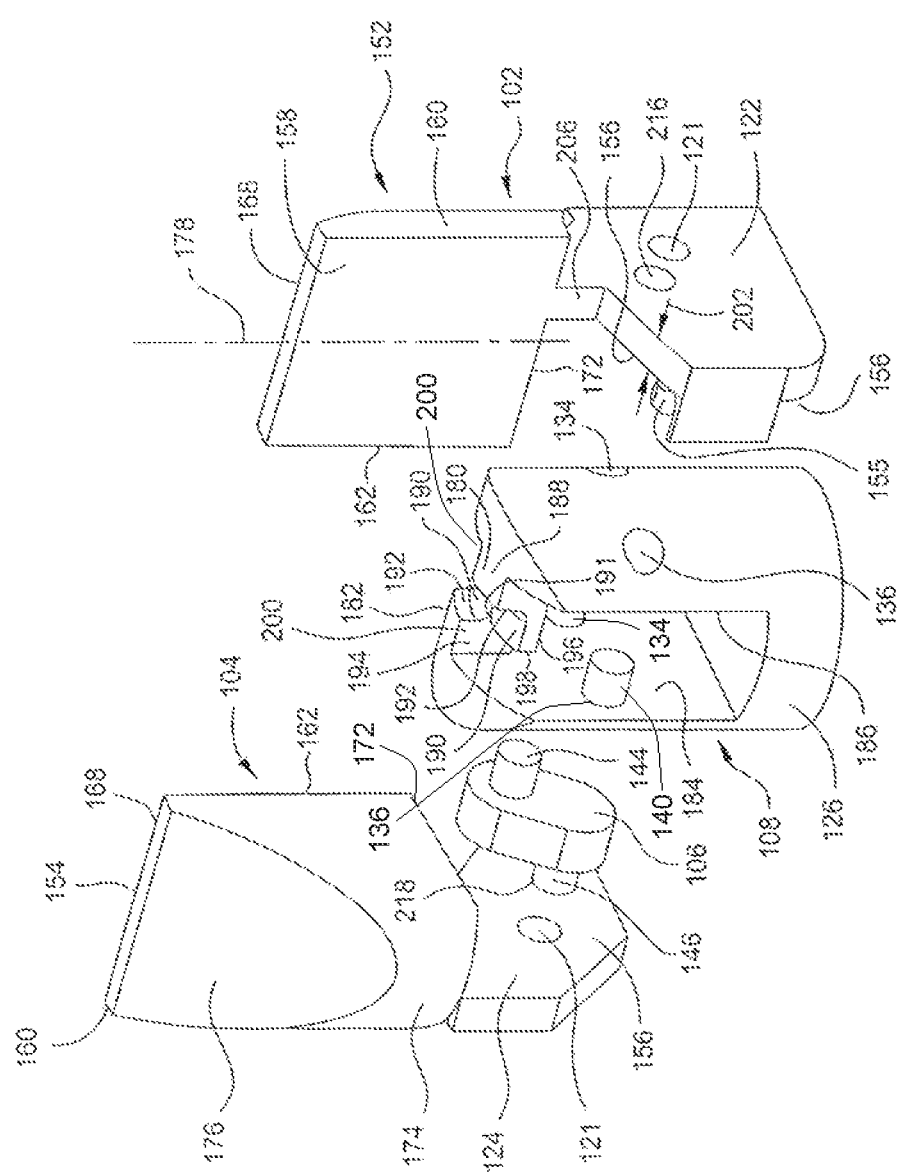

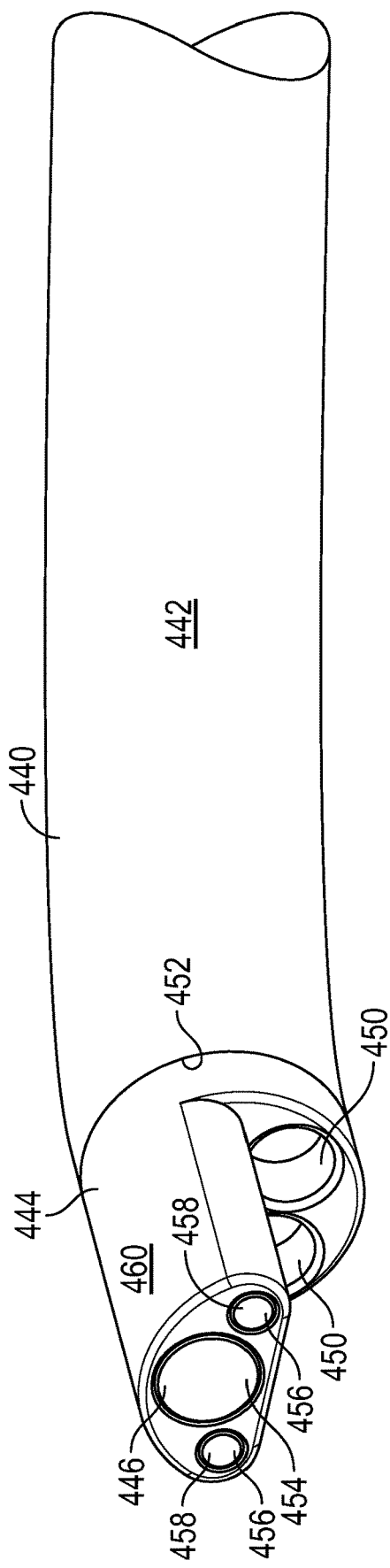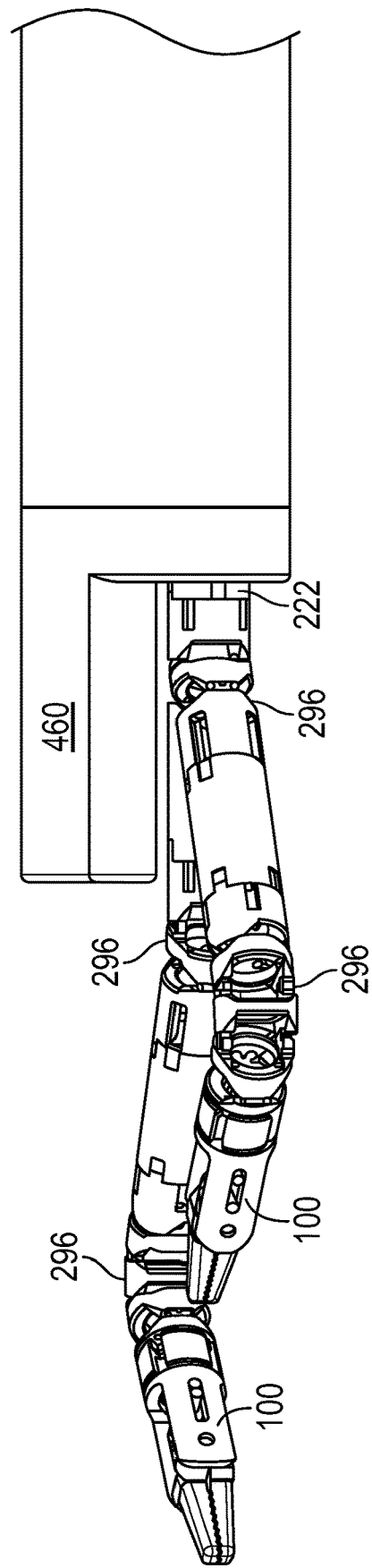

END EFFECTOR AND END EFFECTOR DRIVE APPARATUS

CROSS-REFERENCE TO RELATED APPLICATIONS

This Application is a divisional of U.S. patent application Ser. No. 17/013,311 filed on Sep. 4, 2020, which is a divisional of U.S. patent application Ser. No. 16/495,038, filed on Sep. 17, 2019, which is a national stage application under 35 U.S.C. 371 of International Application No. PCT/US2018/066828, filed Dec. 20, 2018, which claims benefit of U.S. Provisional Application Ser. No. 62/612,220, filed Dec. 29, 2017, all of which are incorporated by reference in their entireties.

BACKGROUND

Field

The present specification relates to robotic surgical systems and procedures used for minimally invasive surgery. More specifically, the present specification relates to the field of robotic controllers and end effectors useful for use in minimally invasive surgery.

Description of the Related Art

Endoluminal surgical instruments are known having at least one end effector extending from the distal end thereof, which is configured as a four bar linkage to enable the opening and closing of jaws of the end effector, or the manipulation of other portions thereof movable with respect to each other, the operation of which is controlled by pulling on wires connected thereto. The use of a four bar linkage induces size constraints on the width (diameter) of the linkage portion of the end effector, which limits the miniaturization thereof. Additionally, multiple wires are used to manipulate the orientation of the end effector, as well as its opening and closing. These wires extend from the end effector, and through a flexible tubular member to a coupling device. The coupling device is connected to the end of a wire controller which is configured to independently pull individual ones of the wires to effect a motion in or of the end effector. Because the number of wires is large, it has become difficult to properly align the wire controller elements used to pull individual ones of the wires, resulting in intermittent failures of control over the end effector, or an inability to properly connect the individual wires to the wire controller.

SUMMARY

Provided herein is an end effector for a surgical apparatus including a housing having an outer wall and an opening therein, and opposed first and second walls extending along opposite sides of the opening, a first actuator pivotally coupled to the first wall of the housing, a second actuator pivotally coupled to the second wall of the housing, and a coupling disposed within the opening of the housing and between at least a portion of the first and second actuators, the coupling including opposed first and second ends, each end pivotally coupled to a different one of the first and second actuators.

BRIEF DESCRIPTION OF THE DRAWINGS

FIG. 3 is a side view of a the prior art end effector of FIG. 1 in the closed position, including the surrounding body thereof;

FIG. 4 is a side view of a prior art end effector in the open position, including the surrounding body;

FIG. 10 is a side view of the first side of the actuator of the end effector of FIG. 5;

FIG. 11 is an exploded view of the end effector of FIG. 6, showing the internal components thereof;

FIG. 12 is a partial view of the wire used to actuate the end effector of FIG. 6 between the open and closed positions and positions therebetween;

FIG. 22 is an isometric view of the end of an alternative instrument including two surgical instruments and a lighting and camera portion;

FIG. 23 is a side view of the end of the alternative instrument of FIG. 22, wherein a pair of end effectors extend outwardly of the end thereof;

DETAILED DESCRIPTION

End effectors are used in robotic surgery procedures to perform a procedure within a body cavity of a human, mammal or other living entity. The end effector could be actuated remotely from its location, for example, by transmitting a physical force from a location external to the body to a location within the body where the end effector is present.

To minimize the invasiveness of these surgical procedures, the end effector itself must have a minimal diameter on the order of less than one centimeter, more typically on the order of less than 5 or 6 millimeters. Where the end effector is used for a surgical procedure, such as to obtain a tissue sample, to suture an opening shut, to grasp tissue, or the like, it will typically require opposable jaws which can be opened to engage body tissue or a surgical instrument, and closed to engage and hold the instrument or body tissue. Additionally, for cutting, the opposable jaws can include opposed blades, or a blade and an opposed grounded plane surface past which the blade passes, to cut body tissue therewith. In each case, where force is transmitted from a location exterior of the body to the end effector located within the body, the resulting force at the opposed jaws must be sufficient to grasp or cut tissue or grasp another item. The force needed to open and close the opposed jaws with respect to each other is typically provided by either a wire extending from the end effector to a location of the flexible tubular member exterior of the body and a spring return mechanism at the end effector location or integrally located within the end effector, or by a pair of wires, each separately engageable with a portion of the end effector. Additionally, an end effector operable by a single wire which is passed over the circumference of a shaft in the end effector is known. By separately providing a pulling force to one of the opposed ends of the wire or one of the pairs of wires, the end effector is actuatable between the opened, closed, or intermediate positions therebetween.

Figure 1:
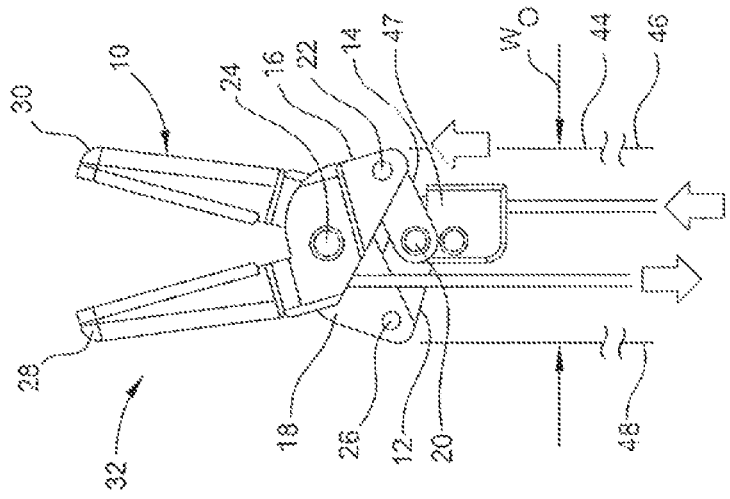
FIG. 1 is a side view of a prior art end effector in the closed position, showing a four-bar linkage without a surrounding body.
Figure 2:
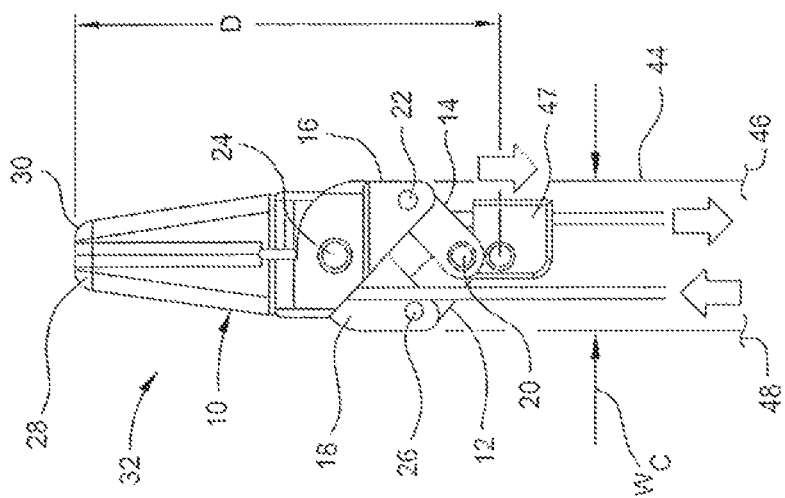
FIG. 2 is a side view of a prior art end effector in the open position, showing a four-bar linkage without a surrounding body.

In the above described wire movement paradigm, the end effector opening and closing mechanism is a four-bar linkage mechanism as shown in FIGS. 1 and 2 herein. In this prior art mechanism, a linkage 10 includes a first bar 12, a second bar 14, a third bar 16 and a fourth bar 18. A first end of the first and second bars 12, 14 are pivotally connected at a first pin 20, which extends through the first ends of the first and second bars 12, 14 but allows the first ends of the first and second bars 12, 14 to rotate thereabout and thus the opposed second ends of the first and second bars 12, 14 to move arcuately thereabout. The second end of the first bar 12 is pivotally connected to a first end of the fourth bar 18 by a fourth pin 26, which extends through the second end of the first bar 12 and the first end of the fourth bar 18, but allows the second end of the first bar 12 and the first end of the fourth bar 18 to rotate thereabout and thus the opposed first end of the first bar 12 and second end of the fourth bar 18 to move arcuately thereabout. The second end of the second bar 14 is pivotally connected to a first end of the third bar 16 by a second pin 22, which extends through the second end of the second bar 14 and the first end of the third bar 16, but allows the second end of the second bar 14 and the first end of the third bar 16 to rotate thereabout and thus the opposed first end of the second bar 14 and second end of the third bar 18 to move arcuately thereabout. The second ends of the third and fourth bars 16, 18 are pivotally connected by a third pin 24 extending therethrough, such that the second ends of the third and fourth bars 16,18 are free to rotate thereabout and their first ends are able to move along an arc thereabout. In the linkage 10 of FIGS. 1 and 2, the second ends of the third and fourth bars 16, 18 are integrally formed with tool extensions 28, 30, here configured as opposed sides of a clamp 32, which in FIG. 1 is shown in the closed position, and in FIG. 2 is shown in the open position.

Referring now to FIGS. 3 and 4, the pin 20 coupling together the first ends of the first and second bars 12, 14 extends outwardly from the opposed sides of the first and second bars 12, 14, and into opposed slots 36 (only one shown) in an end effector housing 34. Additionally, the pin 24 coupling the third and fourth bars 16, 18 extends outwardly from the opposed sides of the third and fourth bars 16, 18, and into a generally round opening 38 (only one shown) in the end effector housing 34. A longitudinal axis 40 passing along the center of the longer direction of the slot 36 is configured to pass through the center 42, or nearly the center 42, of the generally round opening 38. The generally round opening 38 is sized such that the pin 24 is substantially restricted to move radially in the slot 36, but can move rotationally therein.

A wire 44 extends from a first wire end 46 thereof at a location distal to the linkage 10, here at a location exterior to a body, such as a manipulating device on a proximal end of a flexible tubular member located exteriorly of a body when the linkage 10 is disposed within a body, into the end effector housing 34 at a location thereof distal from the tool extensions 28, 30, alongside one side of pin 20, over pin 24, back past a second side of pin 20 and outwardly of the end effector housing 34 to a second wire end 48 thereof at the location distal of the body within which the linkage 10 is present. To transfer the motion of the wire 44 to the four-bar linkage 10, an actuator clamp 47 is clamped over wire 44 and is pivotally or loosely connected to the pin 20 coupling together the first and second bars 12, 14.

To actuate the linkage 10, here to move tool extensions 28, 30 of the clamp 32 between the closed position of FIGS. 1 and 3 and the open position of FIGS. 2 and 4, the wire 44 is moved along its length direction over the pin 24, by pulling, pushing, or pulling and pushing the opposed ends 46, 48 of the wire to move the clamp 47 toward or away from the pin 24. Because pin 24 is secured against movement in the direction of the longitudinal axis 40, and the clamp 47 is connected to pin 20, by moving the wire along the length direction of the wire 44, the pin 20 is moved in the slot 36 along the longitudinal axis thereof, and this motion causes the four-bar linkage to move the tool extensions 28, 30 of the clamp 32 between the closed position of FIG. 1 to the open position of FIG. 2. Pulling the wire on the second end 48 thereof in the direction away from the linkage 10 causes the clamp 47 to move in the direction of pin 24, pushing first and second bars 12, 14 in the direction of pin 24, and resultantly pushing against third and fourth bars 16, 18 toward pin 24. As pin 24 is secured against moving in the longitudinal direction of the slot 36, this causes the connection of first and fourth bars 12, 18 at fourth pin 26, and the connection of second and third bars 14, 16 at second pin 22, to move outwardly from the longitudinal axis 40 of the slot 36. As the third and fourth bars 16, 18 are pivotally connected at fourth pin 24, an equal and opposite motion than that of the portion of them surrounding pins 22, 26 occurs at the distal ends of tool extensions 28, 30. Thus, pulling on the end 48 of the wire 44 causes the four-bar linkage 10 to actuate the tool extensions 28, 30 to the open position of FIGS. 2 and 4. Pulling of wire at the first end 46 in the direction away from the end effector causes wire clamp 47 to move away from pin 24, and thereby cause the pins 22, 26 to move inwardly toward the longitudinal axis 40 of the slot 36 and simultaneously away from the pin 24, and thus an equal and opposite motion imparted to the tool extensions 28, 30 causes them to move toward the closed position shown in FIGS. 1 and 3.

The structure of the four-bar linkage 10 requires a relatively long, and wide, housing 34 within which the operative elements of the linkage 10, specifically the bars 12-18, the pins 20, 24, the slot 36 and the opening 38 must be secured. In use, the end effector is located at one end of a flexible tubular member or another introduction mechanism within which the wire 44 extends, such that the end effector housing 34 is mounted to an end thereof. The length 50 of the end effector housing 34, and the flexibility of the flexible tubular member immediately adjacent to the end effector housing 34, determines the minimum radius of the arc through which the width 52 of the end effector housing 34 will change when operated by an external drive mechanism. The width 52 of the end effector housing 34 is dictated by the maximum width Wo of the four-bar linkage 10 which occurs when the tool is at its maximum opening position as shown in FIGS. 2 and 4, as compared to the width We which occurs when the tool is in the closed position of FIGS. 1 and 3, wherein the outer diameter or maximum width of the end effector housing 34 is larger than this width Wo, as a portion of the end effector housing 34 extends over the four-bar linkage 10. The width 52 of the end effector housing 34 thus limits the opening area into which the end effector can be introduced, and the size of the opening in the body which must be opened to introduce the flexible tubular member having the linkage 10 thereon. The lengths of the bars dictate the width Wo, and also dictate the maximum opening angle of the tool extensions 28, 30, about third pin 24. Thus, practical limitations on the size of the end effector housing limit the opening angle of the tool extensions 28, 30. These sizes limit the functionality and utility of the four-bar linkage 10.

To move the wires 44 and thus enable movement of the four bar linkage 10 in the prior art, the proximal end of the flexible tubular member on the distal end of which is mounted the end effector housing 34 containing the four bar linkage 10 is connected to an adaptor coupling 252 (see e.g. FIG. 15) which is releasably connectable to controllable drive mechanism, and includes it includes therein a plurality of wire magnets M (FIG. 19), each coupled to the proximal ends of a wire 44 extending through the flexible tubular member from the distal end thereof to the adaptor coupling 252. The magnets M are magnetically coupled to, and thereby are biased into contact with, a magnet pole m' (FIG. 16), which can be a magnet or a slug comprising a ferromagnetic material, which in turn are connected to control wires extending from a controllable drive member. To effect movement of the four-bar linkage 10, one of the two wire ends 46, 48 is pulled in the direction of the controllable drive mechanism directly through this magnetic linkage, resulting in the other wire end 46 or 48 being pulled away from the controllable drive mechanism. In this construct, there is a risk of the magmatic members M, m' becoming separated as the controllable drive mechanism pulls on the wire connected to m', and thus there is a limit, based on the strength of the magnetic attraction between M and m', on the force that can be applied to pull a magnet M toward the controllable drive mechanism.

Additionally, in another prior art construct, the magnets M on the ends of the wires 44 are replaced with a hook mechanism, as is pole m'. In this construct, greater force can be applied to pull the wire ends 46, 48 toward the controllable drive mechanism, but, there is difficulty aligning the respective hooks making it difficult to make the connection of the wire ends 46, 48 to the controllable drive mechanism, and the physical size of the hooks limits the minimum size of the adaptor coupling that can be used.

Referring now to FIGS. 5 to 9, an end effector 100 is provided herein which enables a significant reduction in the overall length and width of the tool movement mechanism over that of a four-bar linkage 10 of the end effector of the prior art shown in FIGS. 1-4, and thus enables a shorter, and thinner, end effector 100. End effector 100 generally includes a first side actuator 102, a second side actuator 104, a coupling link 106, a housing 108 and wire 110 connected to one of the first and second side actuators 102, 104. As with end effector housing 34, the end effector 100 is mounted to the distal end of a flexible tubular member, such that the opposed ends 114, 116 of the wire 110 extend outwardly of the proximal end 221 of the flexible tubular member which is located outwardly of a body to enable manipulation thereof with respect to the end effector 100.

Housing 108 is configured to receive pivot pin ends 122, 124 of the first and second side actuators 102, 104 respectively and the coupling link 106 therein, and includes therefor a base 126, and first and second uprights 128, 130 extending therefrom to form slot 132 (see, e.g. FIG. 6) therebetween. Here, base 126 and uprights 128, 130 are integrally formed and are for example machined from a single piece of biocompatible metal such as stainless steel, or formed of a biocompatible material by an additive process such as three dimensional printing. Each upright 128, 130 includes a pair of pin openings 134, 136 therein, wherein the centerlines of the pin openings 134 in opposed uprights 128 130 are aligned co-linearly across the slot 132, and the centerlines of the pin openings 136 in opposed uprights 128, 130 are aligned co-linearly across the slot 132. A first pivot pin 138 extends from, and is supported in, pin opening 134, and extends into an opening or hole 121 (see FIG. 11) in the pivot pin end 122 of the first side actuator 102. The first pivot pin 138 is sized to interferingly engage with the inner walls of the pin openings 134, to prevent rotation thereof therein, while the hole 121 in the first side actuator 102 is slightly larger than the circumference of the first pivot pin 138, to allow the first side actuator 102 to freely move thereover. Alternatively, the hole 121 in the first side actuator 102 may be slightly smaller than the circumference of the first pivot pin 138, and the pin opening 134 slightly larger in circumference than the first pivot pin 138, to allow the first pivot pin 138 to rotate in the pin opening 134 and first side actuator 102 to move in an arc with respect to the pin opening 134. A second pivot pin 140 extends from, and is supported in, pin opening 136, and into an opening or hole 121 in the pivot pin end 124 of the second side actuator 104. The second pivot pin 140 is sized to interferingly engage with the inner walls of the pin openings 136 to prevent rotation thereof, while the hole 121 through the second side actuator 104 is slightly larger than the circumference of the second pivot pin 140, to allow the second side actuator 104 to freely move thereover. Alternatively, the hole 121 in the second side actuator 104 may be slightly smaller than the circumference of the second pivot pin 140, and the pin opening 136 slightly larger in circumference than the second pivot pin 140, to allow the second pivot pin 140 to rotate in the pin opening 136 and second side actuator 104 to move in an arc with respect to the pin opening 136.

Coupling link 106 is disposed between the pivot pin ends 122, 124 of the first and second side actuators 102, 104 located within the slot 132, and is connected at opposed ends thereof to different ones of the pivot pin ends 122, 124 of the first and second side actuators 102, 104 by first and second pins 144, 146. The first pin 144 extends from the first end of the coupling link 106 and into the pivot pin end 122 of first side actuator 102 at a location between the connection of the pivot pin 138 with the first side actuator 122 and the centerline 150 of the end effector, and the second pin 146 extends from a second end of the coupling link 106 and into the pivot pin end 124 of second side actuator 104 at a location between the connection of the pivot pin 140 with the second side actuator 104 and the centerline 150 of the end effector 100. Within the slot 132, a slight gap remains present between the sides of the coupling link 106 and the adjacent facing surfaces of the pivot pin ends 122, 124 of the first and second side actuators 102, 104, such they can move in a relative sliding motion with respect to each other with minimal interference from each other.

Each of first and second side actuators 102, 104 include a tool portion 152, 154 respectively, here each tool portion 152, 154 making up one half of a pair of clamping jaws, which is connected to the respective pivot pin ends 122, 124 of each of first and second side actuators 102, 104. The first and second actuators 122, 124 here comprise a continuous piece of material forming a pivot pin end 122 and tool portion 152, as well as pivot pin end 124 and tool portion 154, and are for example each machined from a single piece of biocompatible metal such as stainless steel, or formed of a biocompatible material by an additive process such as three dimensional printing. As shown in FIG. 11, each end tool portion 152, 154 is bounded by spaced apart, here generally parallel to one another, side walls 160, 162, an end wall 168 extending across the distal end thereof terminating at the opposed ends thereof at side walls 160, 162, a base wall 172 extending generally parallel to end wall 168 and terminating at the opposed ends thereof at side walls 160, 162, and a front, gripping face 158 which is bounded by the side walls 160, 162, end wall 168 and base wall 172. On the side of the tool portions 152, 154 opposite of the gripping face 158, side walls 160, 162 extend rearwardly along an arch shaped contour to meet at the rear end 174 of each tool portion 152, 154 adjacent to base wall 172, and a generally flat chamfer 176 extends from end wall 168 in the direction toward the base wall 172 and away from the gripping face 158, and ends at side walls 160, 162 before reaching base wall 172. Pivot pin ends 122, 124 extend from base wall 172 generally parallel to, and offset in the direction of side wall 160 from, the centerline 178 of the gripping face 158. As a result of this offset, the coupling link facing walls 156 of the pivot pin ends 122, 124 face one another when mounted in the slot 132 of housing 108 by a distance slightly greater than the coupling link 106, such that the coupling link 106 can be located therebetween and the afore-described relative sliding motion of the sides of the coupling link 106 with respect to the coupling link facing walls 156 of the tool portions 152, 154 is unrestricted.

Here, the end effector 100 is configured such that each first and second actuators 102, 104, are of the same shape and size, such that they are substantially identical, interchangeable, and when assembled into the housing 108 of the end effector, show mirror symmetry to each other across the centerline 150, except first side actuator 102 includes an additional wire securing recess 155 along the coupling link 106 facing wall 156 of the pivot pin end 122 thereof as shown in FIGS. 10 and 11, and the locations of the openings therein to receive pins may be different. Here, wire securing recess 155 is provided as a wire slot formed between two bosses 157, 159 extending outwardly of the coupling link 106 facing wall of the pivot pin end 102 at a location thereon distally spaced from the blend thereof into the tool portion 152, and also outside of the location where the coupling link 106 must move during actuation of the tool portions 152, 154 of the end effector 100 as will be described further herein.

Referring now to FIG. 11, the housing 108 further includes a pair of wire guides 180, 182 extending from the slot facing walls 184, 186 of the housing 108 and toward each other to close the gap between the slot facing walls 184, 186 at a location across the slot 132 distal from the base 126. Each of the wire guides 180, 182 are mirror symmetric across an imaginary plane extending along the center of the slot 132 parallel to the slot facing walls 184, 186, and wire guide 180 is offset along the slot facing wall 184 in the direction of pin openings 134, whereas wire guide 182 is offset along the slot facing wall 186 in the direction of pin openings 136. Each wire guide 180, 182 includes an upper wall 188 extending over the slot 132, which terminates in a contoured wall 192 extending therefrom in the direction of the slot and bending in the direction of the opposed slot facing wall 184 or 186, and a wire bearing surface 190 extends from the contoured wall to an inner end wall 198 forming the inner terminus of the respective wire guide 180, 182 in the slot 132. In each of wire guides 180, 182, the distance from a slot side wall 184, 186 to the end wall 198 of the wire guide 180 or 182 extending therefrom is more than one-half the spacing between the slot side walls 184, 186, and the distance from a slot side wall 184, 186 to the upper end of an upper wall 188 of the wire guide 180 or 182 extending therefrom is less than one-half the spacing between the slot side walls 184, 186. The resulting spacing or gap between the upper walls 188 of the wire guides 180, 182 in the direction across the slot 132 between the slot side of the facing walls 184, 186 thereof is thus slightly greater than the diameter of the wire 110. Thus, the upper walls 188, contoured walls 192 and wire bearing walls 190 together form a trough-like recess 191 to guide the wire 110 as it is moved to open and close the tool end of the end effector 100. Each wire guide 180, 182 also includes a side wall 194, each side wall 194 of one wire guide 180 or 182 facing in an opposite direction than the sidewall 194 of the other wire guide 180 or 182, such that the adjacent portion of the slot of the facing wall 184 or 186, and the end wall 198 of the other of the wire guides 180, 182, form a generally rectangular recess 200. The width of the recess 200 between an end wall 198 and a facing slot side wall 184, 186 is slightly larger than the width 202 of the pivot pin ends 122, 124. Additionally, the planes formed of each of the generally flat side walls 194 are, or are nearly, aligned to each other and co-planar. An extension wall 206 on the pivot pin ends 122, 124 is formed as a generally coplanar extension of the gripping faces 158. As a result, the side walls 194 form a limiting wall to limit the movement of the gripping faces 158 toward each other. Additionally, the base walls 172 of the first and second actuators 102, 104 are configured to cooperate with the trough-like recess 191 to form a tunnel or conduit which bounds the portion of the wire 110 in the trough-like recess 191 on all sides. When the first and second actuators 102, 104 are in the closed position of FIGS. 5, 6 and 8, the base walls 172 of the first and second actuators 102, 104 are located directly over the trough-like recess 191. When the first and second actuators 102, 104 are in the fully opened position of FIG. 7, the base walls 172 of the first and second actuators 102, 104 are spaced from the trough-like recess 191 equidistant from the centerline 150 of the end effector 100.

Referring to FIGS. 10 and 12, the wire 110 hereof includes a slug 208 formed thereon, which provides a larger diameter portion of the wire 100. Correspondingly, the wire securing recess 155 includes an enlarged width region 208a, having generally rounded detents 210 facing each other across the enlarged width region 208a. The volume of the slug 208 on the wire 110 is larger than the volume of the portion of the wire securing recess 155 provided between the detents 210, and thus by pressing the slug 208 into the volume of the enlarged width region 208a of the wire securing recess 155 at the location of the detents 210, the wire 110 can be secured against movement with respect to the wire securing recess 155. Alternatively, wire 110 may include two slugs spaced from each other by the length of the wire securing recess 155, whereby a slug is located on either side of the wire securing recess, or a single slug which is pulled into the wire securing recess and maintained therein by friction. Additionally, instead of a single wire-passing through the wire securing recess 155, two different wire ends may be secured at different locations of the wire securing recess 155, such as by providing slugs at the ends and locating them within the same, or different recesses 210, or by providing a wire securing recess 155 on each of the first and second actuators 102, 104, and passing each wire end over the wire guide 180,182 before connecting it to a corresponding one of the wire securing recesses 155.

Figure 5:
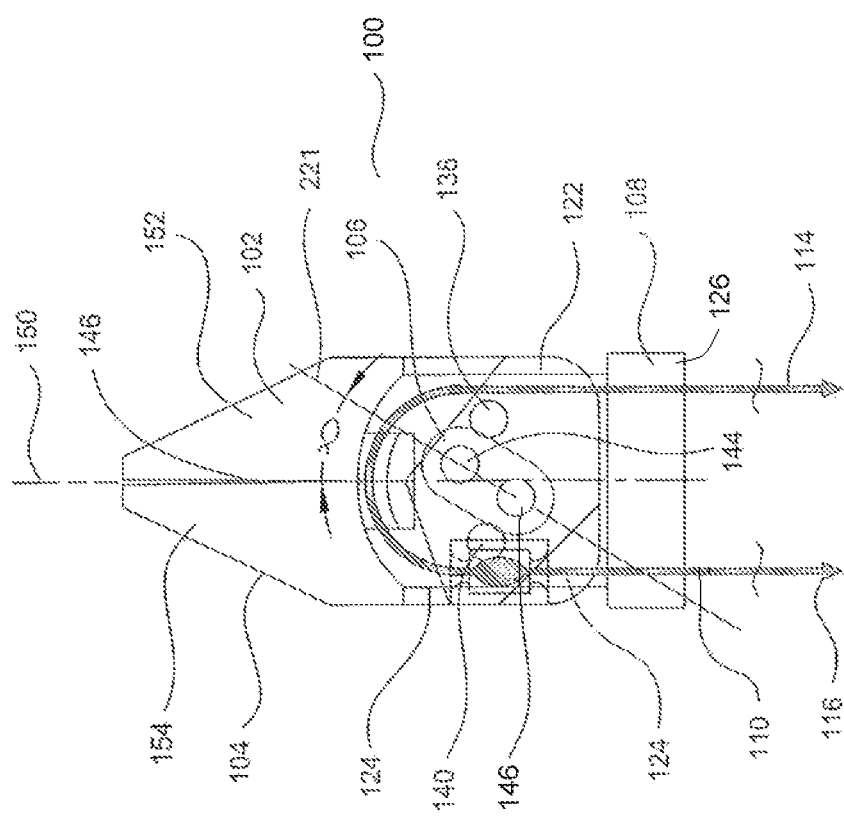
FIG. 5 is a side view of the end effector hereof, showing the internal linkages thereof.
Figure 7:
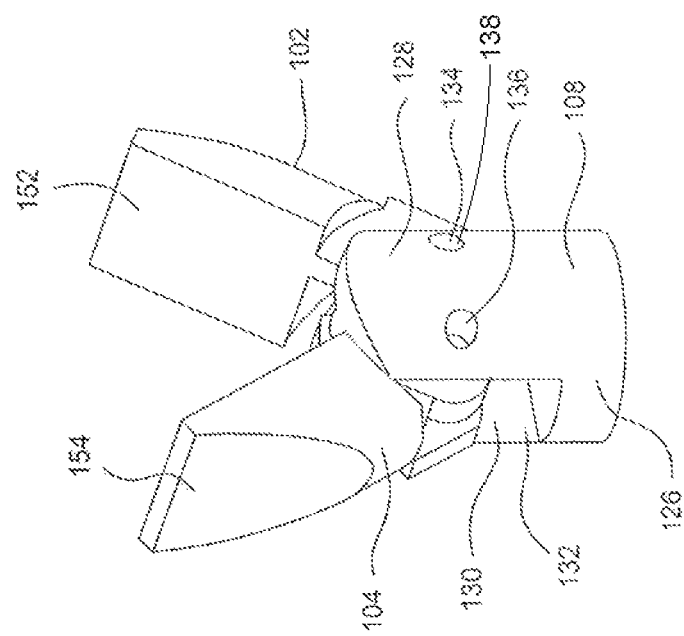
FIG. 7 is an isometric view of the end effector of FIG. 5 in the open position.
Figure 6:
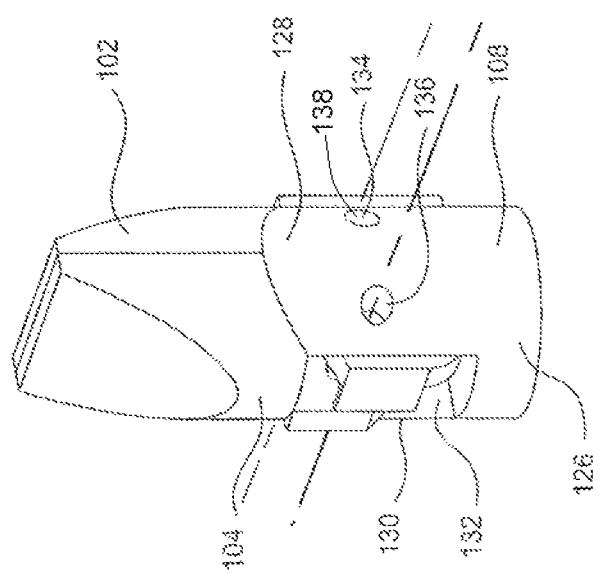
FIG. 6 is an isometric view of the end effector of FIG. 5.
Figure 9:
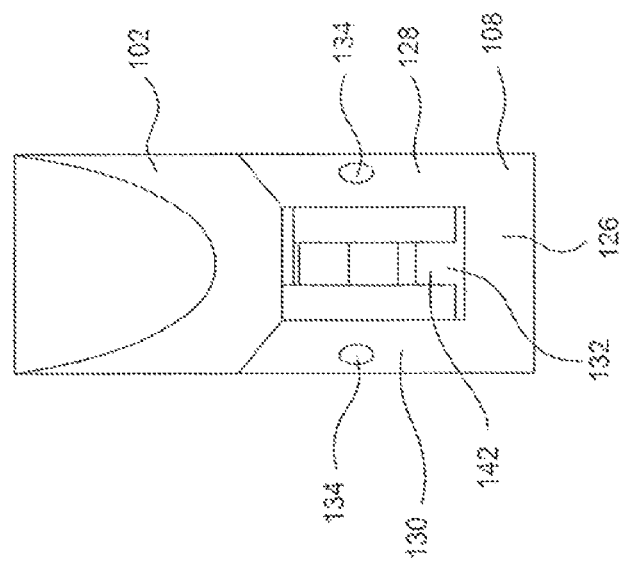
FIG. 9 is a side view of the end effector of FIG. 5 rotated 90 degrees from the view of FIG. 8.
Figure 8:
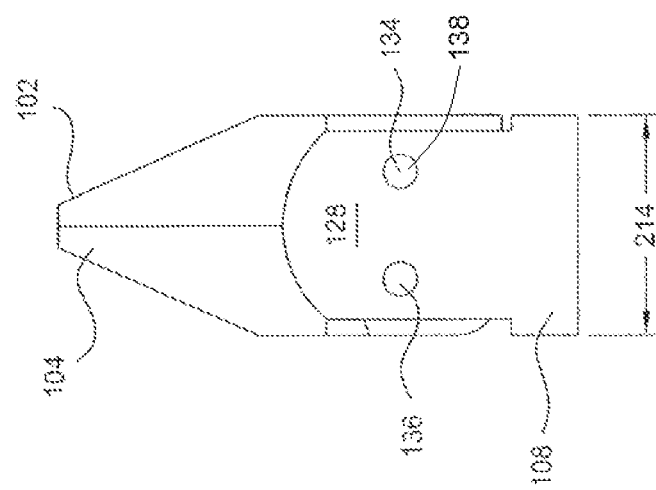
FIG. 8 is a side view of the end effector of FIG. 5.

Referring to FIG. 5, to operate the end effector 100, as described previously herein, pulling the first end 114 of the wire 110 away from the end effector 100 while either allowing the second end 116 of wire to move toward the end effector 100, or actively releasing it toward the end effector 100 at the same rate that first end 114 is being pulled away from the end effector 100, the tool portions 152, 154 of the end effector will move away from each other from the position of FIGS. 5, 6 and 8 to that of FIG. 7, and by reversing the actions of pulling and releasing of the wire ends 114, 116, the tool portions 152, 154 of the end effector will toward each other from a position of FIG. 7 to that of FIGS. 5, 6 and 8. In the end effector 100, this motion of the tool portions 152, 154 is accomplished by the use of the coupling link 106, and as a result, the length 212 of the housing 108 of the end effector 100 incorporating the coupling link is shorter than the length 50 of the end effector housing 34 of the prior art shown in FIG. 4, and the width 214 of the housing 108 of the end effector 100 incorporating the coupling link is smaller than the width 52 of the end effector housing 34 of the prior art shown in FIG. 3.

The openings 216, 218 in the pivot pin ends 122, 124, respectively, are located with respect to the opening or hole 121 therein which receives the first or second pivot pin 138, 140, to ensure that the above described motions of the wire 110 ends 114, 116 result in the opening and closing of the tool portions 152, 154 as described above. As a result, in the closed position of the tool portions 152, 154 as shown in FIG. 5, an imaginary line extending through the coupling link 106 and through an extension of the center lines of the first and second pins 144, 146 extending from opposite sides of the coupling link 106 forms an acute angle α with respect to the end effector 100 centerline 150, and the center of the circumference of each of the first and second pins 144, 146 is located on opposite sides of the center line 150. In the position of the tool portions 152, 154 as shown in FIG. 7, each of the first and second pins 144, 146 is again located on opposite sides of the centerline 150, and is spaced further therefrom. However, the location of the first pivot pin 138 with respect to the first pin 144 of the coupling link 106, and the location of the second pivot pin 140 with respect to the first pin 144 of the coupling link 106, are fixed. Thus, rotational motion of the first pin end 122 about first pivot pin 138 results in an equal and opposite rotational motion of the second pin end 124 about the second pivot pin 140. By fixing the wire to be connected to one of the pivot pin ends 122, 124, here the pivot pin end 122, upon pulling of the end 114 of the wire 110, the slug 208 on the wire 110 pulls the wire securing recess 155, and thus the end of the pivot pin end 122 furthest from the gripping face 158 of the first tool portion, in the direction of the wire guides 180, 182. This motion is transmitted through the first pin 144 of the coupling link 106 to the second pin 146 of the coupling link 106 and into pivot pin end 124, causing it to rotate about second pivot pin 140 such that the end thereof distal from the gripping face 158 likewise moves in the direction of the wire guides 180, 182, resulting in the gripping faces 158 moving away from each other by an equal arcuate movement. Reversing the pulling of the wire 110 to pull the second end 116 thereof likewise results in equal, and opposite, motion of the gripping faces 158.

Figures 13, 14:
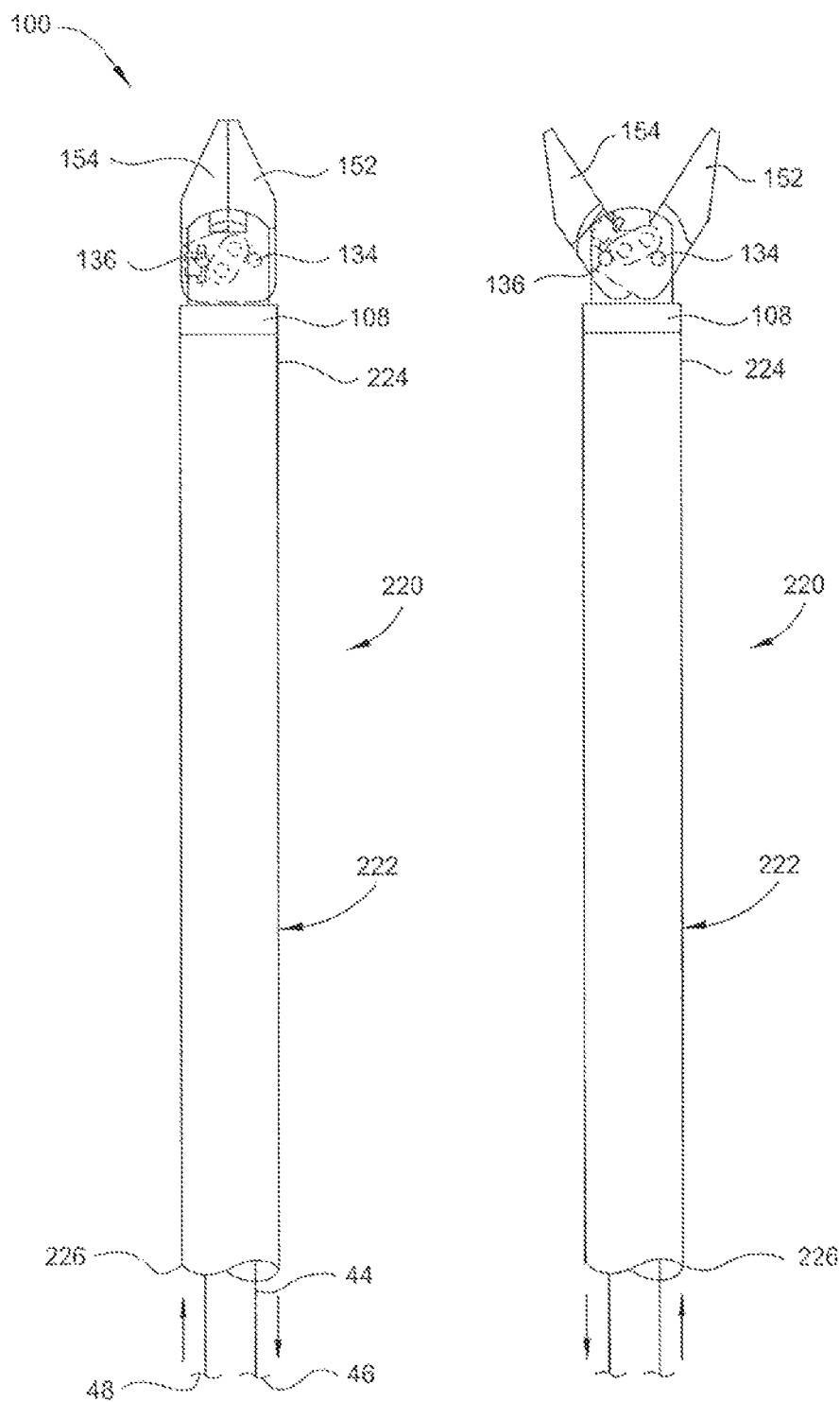
FIG. 13 is a side view of a surgical instrument having the end effector hereof, wherein the end effector is in the closed position.
FIG. 14 is a side view of a surgical instrument having the end effector hereof, wherein the end effector is in the open position.

Referring now to FIGS. 13 and 14, end effector 100 is shown in a portion of a surgical instrument 220, wherein the end effector 100 is mounted to a first open end 224 of a flexible tubular member 222, through which the wire 44 extends within the hollow interior thereof from the first wire end 46 thereof distal from the end 226 of the flexible tubular member 222 distal from the end effector 100, through the end effector 100 where it is connected to the wire securing recess 155 along the coupling link 106 facing wall 156 of the pivot pin end 122 of first side actuator 102 (FIGS. 10 to 12) and then back through the hollow interior of the flexible tubular member 222 to second wire end 48. By pulling wire on the first end 46 away from the end effector 100 while releasing wire end 48 inwardly of the flexible tubular member 222 or allowing it to move inwardly of the flexible tubular member 222, the end effector is moved toward and ultimately to the closed position of FIG. 13. By pulling wire on the second end 48 away from the end effector 100 while releasing wire on the first end 46 inwardly of the flexible tubular member 222 or allowing it to move inwardly of the flexible tubular member 222, the end effector is moved toward and ultimately to the open position of FIG. 14. The flexible tubular member 222 is a generally hollow, bendable and steerable tube or lumen, and thus it can be used in a robotic surgical system to direct the end effector 100 to a desired location within a body, to there allow the end effector 100 to spread apart adjacent body tissue, grasp an object or perform another operation. Likewise, the tool portions 152, 154 of the end effector 100 can be configured as a pair of blades or cutting elements, or a cutting element and a ground portion to the side of which the cutting element passes to slice body tissue. The pulling and releasing of the wire 44 of the end effector 100 is used to open and close the blades, or the blade ground portion combination, to operate the end effector 100.

Figure 15:
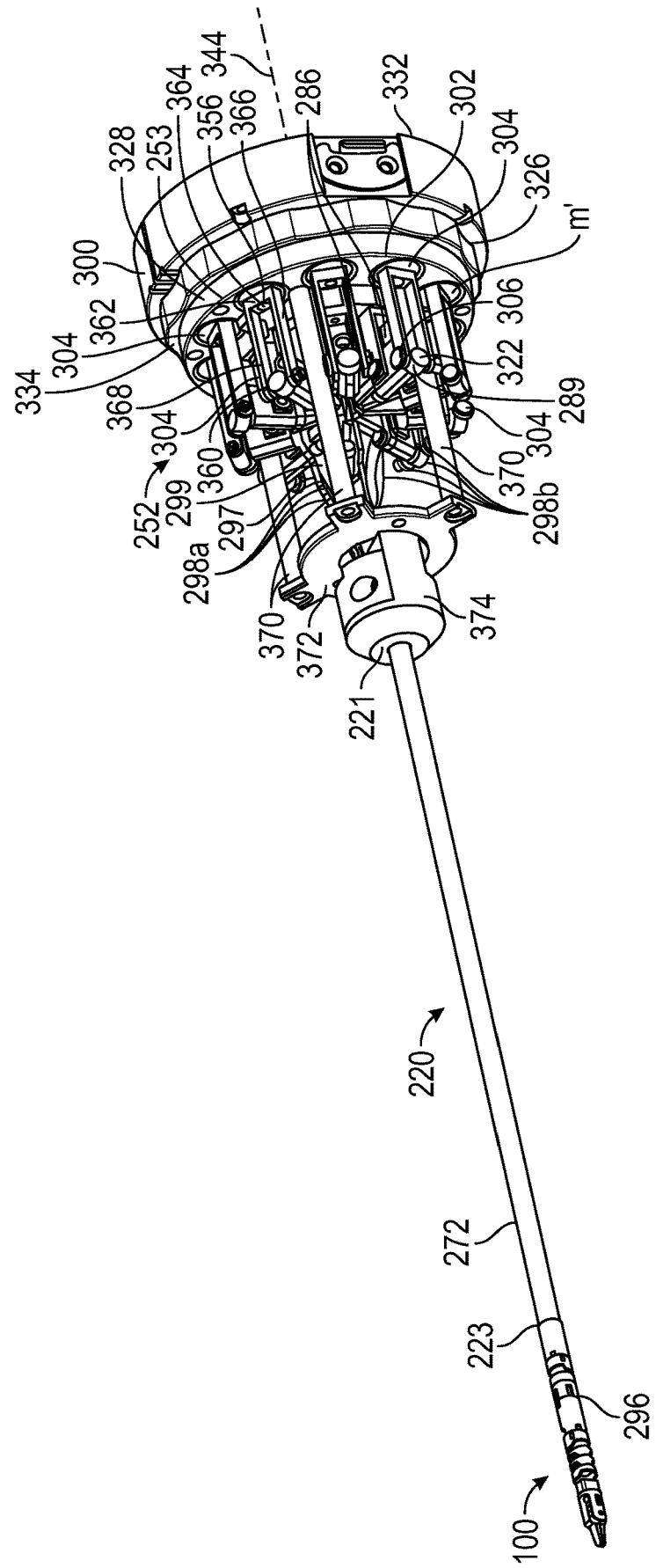
FIG. 15 is an isometric view of a surgical instrument hereof.
Figure 16:
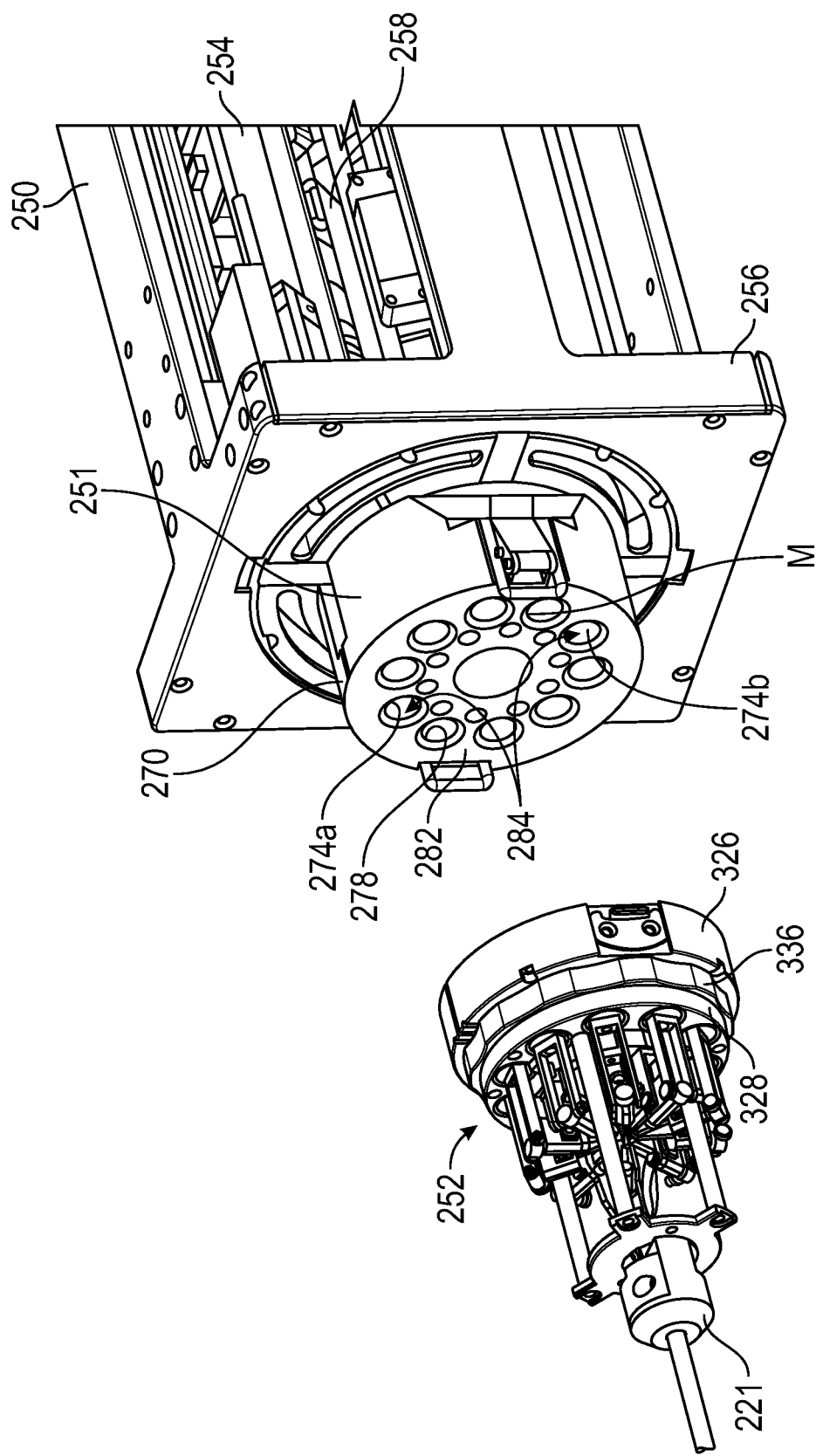
FIG. 16 is an isometric view of the surgical instrument spaced from a drive housing used to operate and move the surgical instrument.
Figure 17:
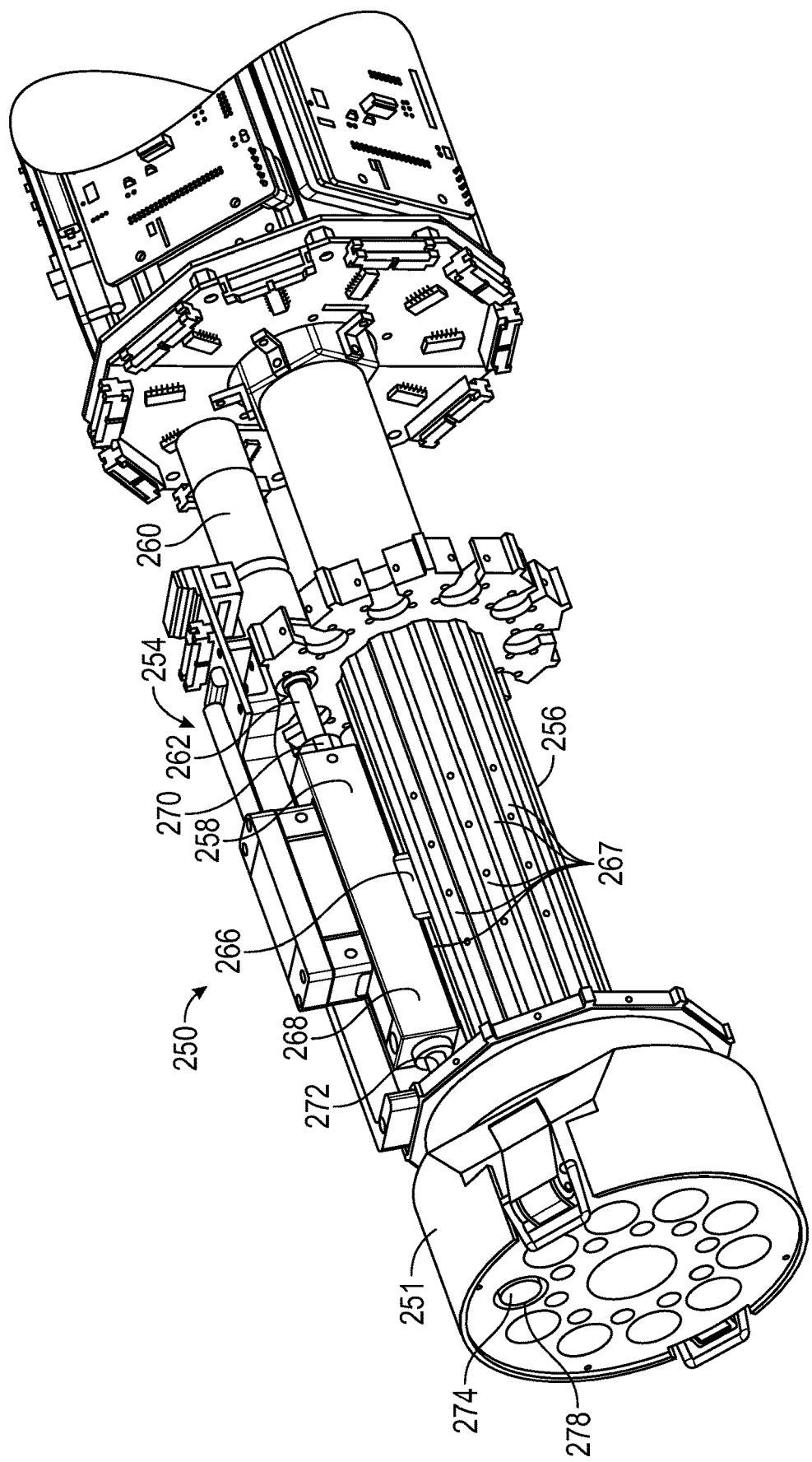
FIG. 17 is a partial isometric view of the controllable drive mechanism housed in the housing of FIG. 16.

Referring now to FIGS. 15 and 16, there is shown the surgical instrument 220 configured to be releasably mounted on a controllable drive mechanism 250 (FIG. 17). Herein, the surgical instrument 220 includes the flexible tubular member 222 having the end effector 100 mounted to the distal end thereof, and an adaptor coupling 252 connected to the proximal end 221 of the flexible tubular member 222. As will be described herein, the adaptor coupling 252 is releasably connectable to the controllable drive mechanism 250 by being locating on a boss 251 extending therefrom, and includes therein a plurality of wire actuation members which are selectively moveable with respect to the adaptor coupling 252 under the control of the controllable drive mechanism 250. The flexible tubular member 222 is configured to include, on an end thereof, a one or more degree of freedom controllably bendable coupling 296, and the movement of the coupling 296 in a bending movement, as well as the control of the operation of the end effector 100, is accomplished using wires 297 which extend between the distal end 223 of the flexible tubular member 222, where the bendable coupling 296 and the effector 100 at the distal end thereof are located, and a proximal end 221 of the flexible tubular member 222, where the ends, i.e., wire ends 298a, b of the wires 297 (having wire ends 46 and 48 of FIGS. 5 to 11, for example) are accessible. Each wire 297 used for control and positioning of the end effector 100, or the bendable coupling 296, may comprise a wire 297 having opposed wire ends 298a,b accessible at the proximal end 221 of the flexible tubular member 220. Here, ten wires having the ten wire ends 298 extending outwardly of the proximal end 221 of the flexible tubular member 222 are used, wherein each of five pairs of wire ends 298a,b are connected to the same portion of the bendable coupling 298, the end effector 100, or another flexible tubular member distal end component such that pulling of one wire end of a pair 298a,b with respect to the distal end 221 of the flexible tubular member 222, results in equal and opposite motion of the other wire end 298a,b with respect to the distal end 223 of the flexible tubular member 222. In FIG. 15, ten total wire ends 298, comprising five ends 298a, and five ends 298b, are present, and each wire end 298a is coupled, through the end effector 100 or bendable coupling at the distal end 223 of the flexible tubular member 222, to the other wire end 298b of the same wire 297. Each of the wires 297, here five wires 297 pass through one of the bendable coupling 296, the end effector 100, or both, and return to the proximal end 221 of the flexible tubular member 222, or, each of the wires 297 extend only between the proximal end 221 and the end effector 100 or bendable coupling 296, but a pair of such wires connect to each of the end effector or an element of the bendable coupling, such that they are associated in pairs. Selective pulling on the wire ends 298a, b with respect to the proximal end 221 of the flexible tubular member 222 results in a motion of the bendable coupling 296 or the end effector 100, such that the associated or connected wire ends 298a, b accessible at the proximal end 221 of the flexible tubular member 222 are useful to actuate the end effector 100 or the bendable coupling 296.

FIG. 17 shows the controllable drive mechanism 250, with the outer housing thereof removed, and only one lead screw mechanism 254 shown therein, for clarity of understanding. In order to move individual ones of the wire ends 298, for example the wire ends 46, 48 of the wire 297 coupled to the end effector 100 described previously herein inwardly and outwardly of the proximal end 221 of the flexible tubular member 222, each of the wire ends 298a, b, including wire ends 46, 48, are individually coupled to a lead screw mechanism 254 dedicated thereto and located in a housing 256, wherein each lead screw mechanism 254 includes a lead screw housing 258 physically connected to, and grounded against rotation and axial movement by, the housing 256, a motor 260, a threaded shaft 262 configured with outer threads (not shown) thereon, and a connecting bracket 268 having a first connector portion 270 having internal threads into which the threaded shaft 262 extends, an extension member 272 extending distally therefrom in a direction away from motor 260, and a second connector portion 274 at the end of the extension member 272 distal to the motor 260. The connecting bracket 268 is free to move in the axial direction of the threaded shaft 262 as a result of motion imparted thereto by rotational motion of the threaded shaft 262, but is grounded against rotation by being rotationally fixed to the housing 256 through a pawl 266 received in, and axially slidable with respect to, a groove 267 extending inwardly of the outer surface of the housing 256. Herein, ten lead screw mechanisms 254, each having a pawl 266 and a groove 267 uniquely associated therewith, are provided on the controllable drive mechanism 250 evenly circumferentially spaced from one another about the housing 256. The second connector portion 274 extends from the lead screw housing 258 and into a bore 278 in the boss 251 of the drive mechanism 250 (see FIG. 16).

Figure 19:
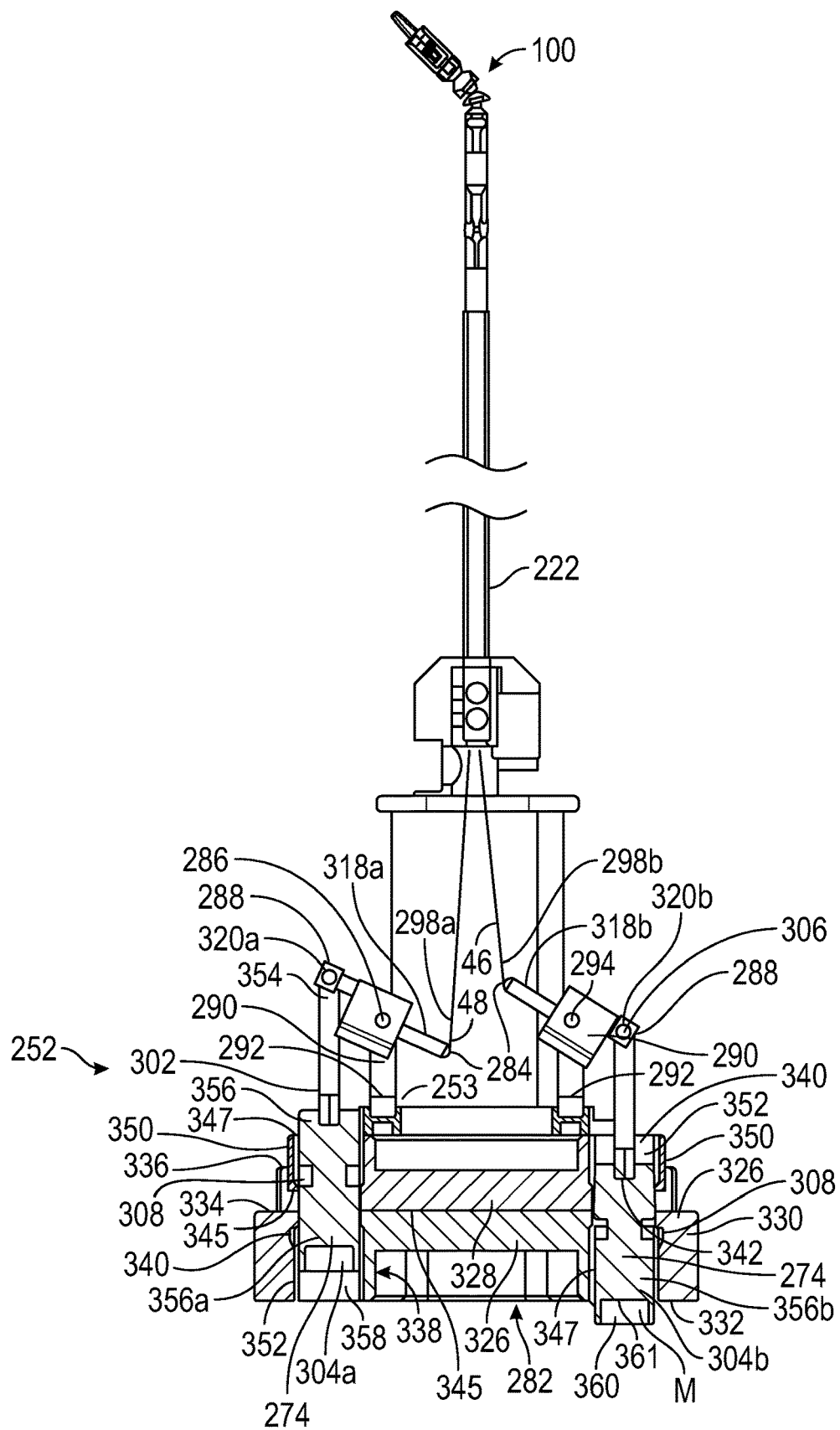
FIG. 19 is a sectional view of the adaptor coupling of the surgical instrument of FIG. 15.

Herein, to overcome the disadvantages of the magnetic coupling or hook connection paradigm of the prior art, the adaptor coupling 252 hereof is modified so that, rather than directly magnetically couple each wire end 298 to a dedicated magnet mounted on the second connector portion 274 and use a pulling action of the second connector portion 274 to pull a wire end in the direction outwardly of the proximal end 221 of the flexible tubular member 222, the wire ends 298, including wire ends 46, 48, as shown in FIG. 19, are each connected to a first end 284 of a lever assembly 286, and the other, second end 288 of the lever assembly 286 is moveable toward or away from the proximal end 221 of the flexible tubular member 222 as a result of movement of the one of the second connector portions 274 associated therewith in the direction toward or away from the proximal end 221 of the flexible tubular member 222, such that motion of the second connector portion 274 toward the proximal end 221 of the flexible tubular member 222 results in pulling of a wire end 46, 48 associated therewith away from the proximal end 221 of the flexible tubular member 222. To enable this lever action, a fulcrum 290 is provided on a fulcrum post 292 extending from a proximal end facing surface 253 of the adaptor coupling 252, the end of which is connected through a hinge pin 294 to a location on the lever assembly 286 intermediate of the opposed first and second ends 284, 288 thereof. By allowing the wire ends 298, here wire ends 46 and 48 to be pulled away from the proximal end 221 of the flexible tubular member 222 by the motion of the lead screws causing the second connector portion 274 to push on one end of the lever through the lever assembly 286, the tolerance match issues where hooks are used for the connection, as well as the issues with pulling a first magnet away from a second magnet in a magnetic coupling to effect wire end 298 motion, are eliminated, because movement of the second connector portion 274 inwardly of the adaptor, i.e., in the direction of the distal end of the flexible tubular member 222, now results in the pulling motion of the wire end 298 by the first end 284 of the lever assembly 286. Therefore, the risk that the magnetic coupling between a magnet and a magnet or slug on a wire end to pull the wire end to affect end effector or the distal end of the flexible tubular member 222 operation will pull apart is eliminated, and the force transmittable to, and the rate of change of that force to pull on the wire end 298, is not effected by pulling a magnet connected to another magnet or slug, but by pushing on a lever to effect pulling of the wire end.

Referring again to FIG. 15, the adaptor coupling 252 is configured as a generally circular cylindrical member, including an attachment portion 300 configured to be releasably mounted to the boss 251 of the controllable drive mechanism 250, and which includes a forward face 302 with respect to which a plurality of plungers 304 which form the second connector portions 272 can be slidably extended or retracted (see FIG. 19, where the plunger 304 to the left is extended, and the plunger 304 to the right is retracted), equal in number to the number of wire ends 298 extending from the proximal end 221 of the flexible tubular member 222, and each of which are connected to the second end 288 one of the plurality of lever assemblies 286 through a second end hinge pin 306.

Figure 18:
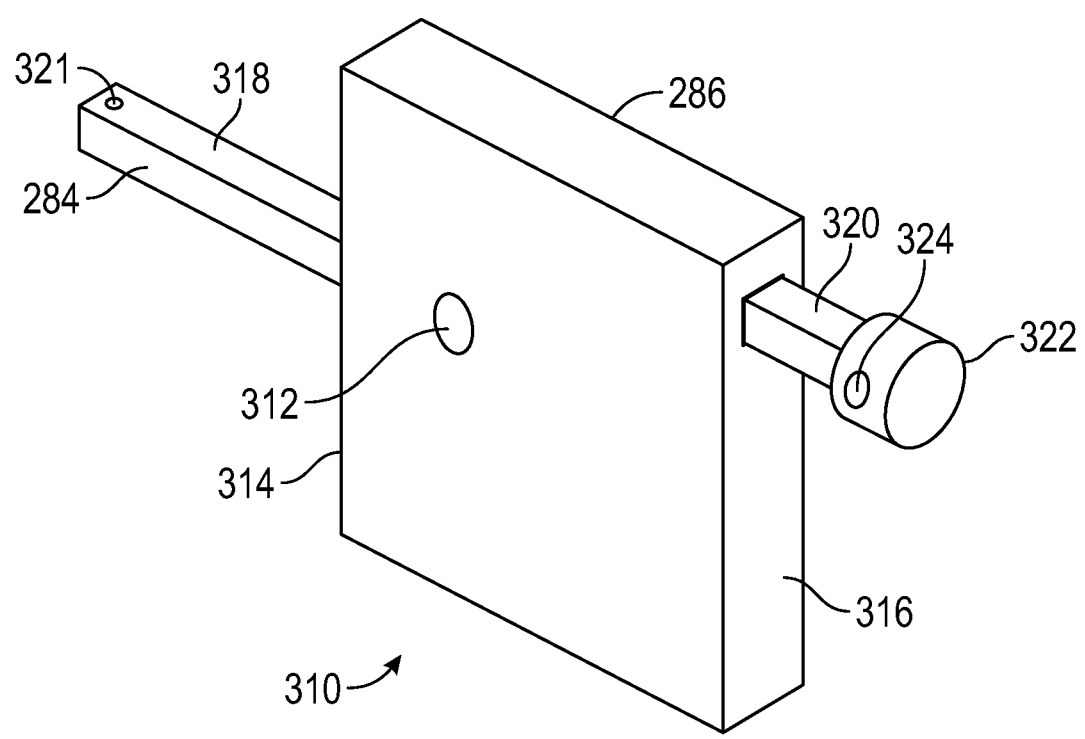
FIG. 18 is an isometric view of a lever mechanism of the surgical instrument of FIG. 15.

As shown in FIG. 18, each of the plurality of lever assemblies 286 include a base plate 310 having a pair of opposed major surfaces through which a hinge pin opening 312 extends, and opposed minor walls 314, 316 including arm bores extending thereinto. A first arm 318 extends from wall 314 to terminate at the first lever end 284, wherein a wire opening 321 extends through the first arm 318 slightly inwardly of the end thereof. The first arm 318 extends from the wall 314 generally perpendicularly therefrom, and the center line thereof extends through the center of hinge pin opening 312. The first arm 318 is press fit, or threaded, into a corresponding opening therefrom in wall 314. A second arm 320 extends generally perpendicularly from the opposed wall 316, and is press fit or threaded into a corresponding opening in wall 316. The longitudinal axis of the second arm 320 is offset from that of the first arm 318 in a direction away from the adaptor coupling 252, and the distal end thereof terminates in an enlarged, generally right cylindrical, bushing 322 through which a pivot pin opening 324 extends.

Referring now to FIGS. 15 and 19, the adaptor coupling 252 is configured of two, interconnected, such as by threaded fasteners, generally right cylindrical bodies, here a base 326 and a cover 328 on which the coupling face 282 is provided. Base 326 includes a main portion 330, having a rearward face 332 and a forward face 334, on which the cover 328 is received, and a circumferential thin walled ferrule 336 is disposed partially between the main portion 330 and the cover 328, and includes a plurality of lock pawls (not shown). A counterbore 338 extends inwardly of the rearward face 332 of main portion 330 generally at the center thereof. A plurality of first bores 340 extend through the base from the forward to the rearward faces 334, 332 thereof, the centers of which are located along a first circumference centered on the centerline 344 of the adaptor coupling 252, and an annular cylindrical bushing 347 is located therein. The first bores 340 are equally angularly spaced from one another along the first circumference.

Cover 328 includes the proximal end facing surface 253, a rear surface 345 on an opposite side thereof, a circumferential wall 350 disposed inwardly of ferrule 336, and a plurality of second bores centered on the circumference 342 and equally angularly spaced from one another along the first circumference. First and second bores have the same diameter, and are angularly aligned along the circumference 342, such that a continuous bushing bore 352 is formed thereby within which an annular cylindrical bushing 347 is disposed. A plurality of the fulcrum posts 292 extend from the proximal end facing surface 253 and terminate at the fulcrums 290 having an opening extending therethrough, through which a pivot pin 285 extending through the hinge pin opening 312 further extends to connect the lever arm to the fulcrum post 292. The plurality of fulcrum posts 292 are equally arcuately spaced from one another about a circumference centered at the center of the adaptor coupling 252, which has a second diameter, smaller than the first diameter. The center of each fulcrum post 292 is positioned along a radius extending from the centerline 344 of the adaptor to a location inwardly of the center of one of the bushing bores 352.

Movement of the wire ends 298 in a direction toward the forward face 302 of the adaptor coupling 252 is caused by movement of the second end 288 of the lever assembly 286 away from the forward face 302. To enable this motion, and perform it in a controllable fashion, each second end 288 of a lever assembly 286 is connected to a plunger 304 dedicated thereto, which is connected to a bushing 356 dedicated thereto and slidingly reciprocally within the annular cylindrical bushings 347 in the bushing bores 352, wherein the rear side 358 of the bushing 356 includes a drive recess 360 extending therein and terminating in a generally circular base wall 361 therein into which the second connector portion 274 at the end of the extension member distal to the motor 260 (FIG. 17) extends. Bushings 356 include a recess 308 extending inwardly of the outer circumference thereof, and the lock pawls on the ferrule 336 are selectively actuatable, by rotation of the ferrule 336, to extend inwardly of the circumferential recesses 308 to limit the stroke of the bushings 356 within the bushing bores 352. Here, the plunger 304 is a generally U-shaped member having a base 362 connected to the center of the upper surface of the bushing 356 with a pin 364 extending therethrough and press fit or threaded into a bore provided therefor in the upper surface of the bushing 356, and a pair of arms 366, 368 (FIG. 15) extending from the opposed ends of the base 362 in a direction away from the bushing 356. Inwardly of the ends of the arms 366, 368 spaced from the bushing 356 are located a pair of aligned openings, such that the second end hinge pin 306 extends through the opening in arm 366, the second pivot pin opening 324 in second arm bushing 322, and the opening in arm 368, to allow the lever assembly 286 to swing thereabout. The plunger, and adaptor can be configured of a metal such as aluminum or steel, of an engineered polymer, or combinations thereof. The bushing 356 and plunger 304 may also be configured as a single piece member, of an engineered polymer or a metal such as aluminum.

The first and second wire ends 46, 48 of wire 44 (FIG. 13) extend from the distal end of the flexible tubular member 222, and each wire end 298a, b, here wire ends 46, 48, is secured in a wire opening 321 in a first arm 318 of a different lever assembly 286, here for ease of understanding, to first arms 318a, 318b. In FIG. 19, second wire end 48 has been pulled away from the proximal end 221 of the flexible tubular member 222 by movement of the first arm 318a, resulting in first wire end 46 being pulled toward the proximal end 221 of the flexible tubular member 222, because the wire ends 46, 48 are opposed ends of the same wire 44, and the wire 44 is fixedly connected to the first side actuator 102 of the end effector 100 at the wire securing recess 155 thereof (FIG. 10), approximately midway between wire ends 46, 48. In these positions of the lever assemblies 286 and the wire ends 46, 48, the end effector 100 is in the open position of FIG. 14. This position was provided as a result of one of the lead screw devices pushing one of the plungers 304a inwardly of the adaptor coupling 252 from the rearward face 332 thereof, to cause the plunger 304a to move to push the second arm 320a of the lever arm away from the adaptor coupling 252, thereby causing the end of the first arm 318a to move toward the forward face 302 of the adaptor coupling 252 and thereby pull the second wire end 48 away from the proximal end 221 of the flexible tubular member 222. This causes the first wire end 46 to be pulled toward the proximal end 221 of the flexible tubular member 222, causing the lever arm of the lever assemblies 286 attached thereto to pivot about the hinge pin 294 on the fulcrum 290, causing the bushing 322 on the second arm 320b thereof to push the end of the plunger 304b attached thereto in the direction of the forward face 302 of the adaptor coupling 252, thereby pushing the plunger 304b in a direction toward the rearward side 332 of the adaptor coupling 252, such that the rear side of the plunger 304b will extend outwardly of the rearward side 332. Reversing this, by actively pushing on the plunger 304b attached to the first arm 318b of the lever assembly 286 attached to the first wire end 46, causes the first wire end 46 to be pulled away from the proximal end 221 of the flexible tubular member 222, thereby moving the jaws of the end effector 100 toward, or to, the position thereof in FIG. 13, and pulling the second wire end 48 toward the proximal end 221 of the flexible tubular member 222, thereby, through the lever assembly 286 attached thereto, pushing the end of the plunger 304a attached thereto toward the forward face 302 of the adaptor coupling 252 and thus the bushing 356 attached thereto inwardly of the adaptor coupling 252, such that the rear end of the plunger 304a extends outwardly of the rearward wall 332.

Herein, lead screw mechanisms 254 (FIG. 17) are dedicated to provide the pushing force to move the second arms 320 of the lever assembly 286 in the direction away from the forward face 302 of the adaptor coupling 252, and that force is transmitted to the wire, here wire 44, to cause the wire end 46 or 48 not being pulled by a second arm 320 in the direction toward the forward face 302 of the adaptor coupling 252, to move in the direction away from the forward face 302 of the adaptor coupling 252 and hence cause the plunger 304 and bushing 356 connected thereto to move in the direction toward or inwardly of the forward face 302 of the adaptor coupling 252.

Using the movement of the wire 44 and the wire ends 46, 48 as an example, a second connector portion 274 (FIG. 17) connected through the connecting bracket 268 to the shaft 262 for linear movement thereof, is located in contact with the circular base wall 361 of the drive recess 360 of the bushing 356b connected to the plunger 304 connected to the second arm of the lever 286 connected to wire end 48 through the second arm 320b thereof (see FIG. 19). Simultaneously, a second connector portion 274a connected through the connecting bracket to a different shaft for linear movement thereof, is located in contact, or nearly in contact, with the circular base wall 361 of the drive recess 360 of the bushing 356a connected to the plunger 304 connected to the second arm of the lever 286 connected to wire end 46 through the second arm 320a thereof. To cause the wire end 46, 48 movements, the motor 254 is connected through the connecting bracket 268 to the second connector portion 274a to move it in the direction toward the motor 254, and a different motor 254 connected through the connecting bracket 268 to the second connector portion 274b to move it in the direction away from the motor 254, and the velocity of the movements of the second connector portions 274a, b with respect to the forward face 302 of the adaptor coupling 252 are the same, but in opposed directions. Because there is no "hard" connection between the second connector portions 274a,b and the bushings 356a, b, the movement of the bushing 356a in the direction of the motor 254 is caused entirely by the pulling on the wire end 46 in the direction of the proximal end 221 of the flexible tubular member 222 as a result of wire end 48 being pulled away from the proximal end 221 of the flexible tubular member 222. Because the movement of the wire end 48 away from the proximal end 221 of the flexible tubular member 222 is a function of the linear movement induced by the other motor 254 thereon through the lever assembly 286, and the motor 254 the second connector portion 274a in the opposite direction at the same velocity, as the construct of all of the levers, bushings and plungers is identical, the bushing 356a will move in the opposite direction as the bushing 356b, but at the same velocity, and as the second connector portion 274a retracts toward the motor 254, the circular base wall 361 of the bushing 356a will follow the second connector portion 274a at the same velocity the as the second connector portion is retracting toward the motor 254a. Upon reversing the motor rotation directions, the same effect will occur, but in reverse. Thus, the need to physically couple the second connector portions 274 and bushings 356 is eliminated, resulting in locating the adaptor on the boss 251 of the controllable drive member 250 without the need for complex alignment therebetween. Also, because the motion of the wire ends 46, 48 is accomplished by pushing the bushings 356a, b to cause an opposite movement of the wire end 46 or 48 and thus the wire 44, there is no risk of decoupling the lead screw motion from the wire 44 during use.

Referring again to FIG. 15, the adaptor coupling 252 includes structures to connect the proximal end 221 of the flexible tubular member 222 thereto. Here, a plurality of posts 370 extend outwardly from the forward face 302 of the adaptor coupling 252, and are connected at their projecting ends to a bridge plate 372 having a coupling 374 of the flexible tubular member 222 connected thereto at a location generally centered over the forward face 302 of the adaptor coupling 252. The wires 298a, b extend from the lever assembly and through the inner bore of the coupling 374 and into the proximal end 221 of the flexible tubular member 222 connected thereto.

Referring again to FIGS. 13 and 14, the end effector 100 herein has a smaller length body, and a smaller diameter or width, compared to a prior art four-bar link end effector housing 34 of FIGS. 1 and 2 having the same operable capability. Thus, the end effector 100 herein enables a more precise positioning of the distal ends of the tool portions 152, 154 and a smaller diameter opening into which the end effector 100 in the closed position will pass. Likewise, the connection paradigm of the wire ends 298 (46 or 48) to the linear actuator used to enable pulling motion on a wire end to move it away from the proximal end 221 of the flexible tubular member 222 is accomplished by a pushing force between a wire end 298 connected portion and a lead screw connected portion, and thus direct pulling of a wire end 298 (46 or 48) by the lead screw connected portion occurs, resulting in a more reliable connection of the wire ends 298 to the drive mechanism therefor.

Figure 20:
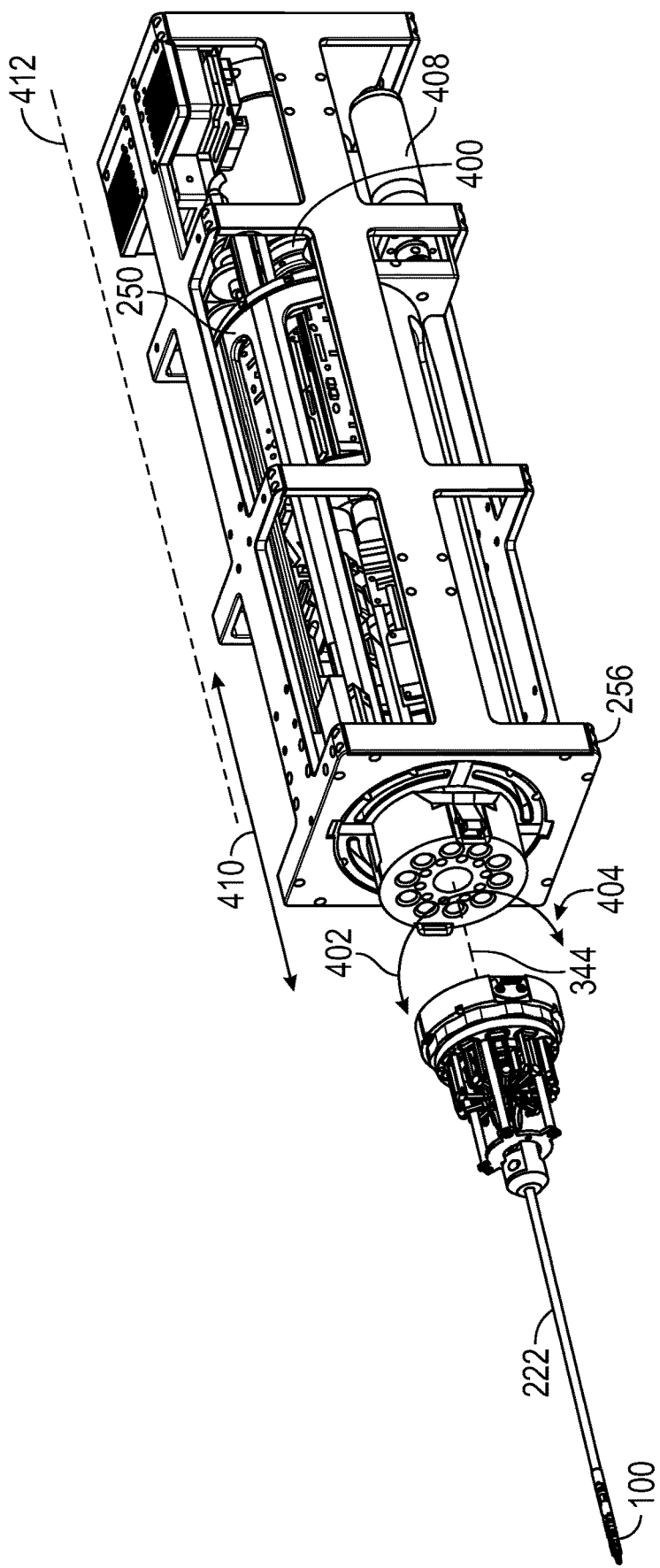
FIG. 20 is an isometric view of the housing and controllable drive mechanism spaced from the surgical instrument.

Referring now to FIG. 20, controllable drive mechanism 250 and thus surgical instrument 220 are moveable in the "x" direction 410 by movement of the housing 256 in the x direction 410 in a further master housing (Not Shown). Controllable drive mechanism 250 is also rotatable, about centerline 344, by a rotating a ring gear 400 connected thereto and driven by rotation of a drive motor 408. This allows controllable rotation of the surgical instrument 100, and the tubular member 222, rotationally in opposite arcuate directions 402, 404. The master housing may also be controllably rotated about axis 412, such that housing 256 therein will move in an orbital arc about axis 412.

Figure 21:
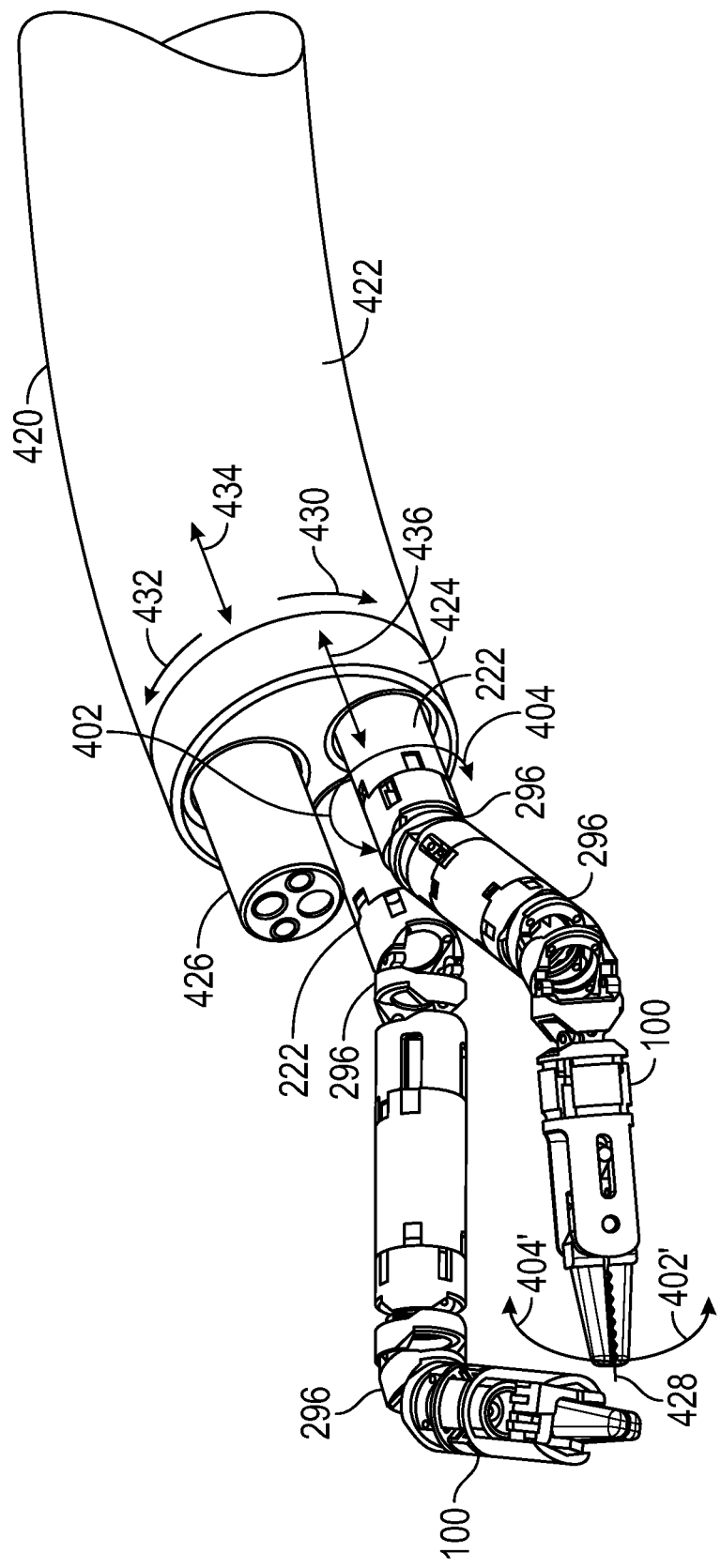
FIG. 21 is an isometric view of the end of an instrument including two surgical instruments and a lighting and camera portion.

Referring to FIG. 21, the end of an instrument 420 is shown, wherein an outer sheath 422 encloses two flexible tubular members 222 and an illumination and camera instrument 426, each of which is extendable from a cap 424 having openings 430 therein through which the tubular members 222 and an illumination and camera instrument 426 are selectively extendable. In FIG. 21 the distal ends of the flexible tubular members 222 extend outwardly of the cap 424, and thus the bendable couplings 296 thereof are positioned outwardly of the outer sheath 422, and the end of the illumination and camera instrument 426 is likewise extended outwardly of the cap 424 and thus of the sheath 422.

If controllable drive mechanism 250 is rotated in the directions 402, 404 about centerline 344, the distal end of the flexible tubular members 222 likewise rotate at the cap 424 in direction 402, 404. If the end effector 100 is positioned as shown in FIG. 20. It will likewise rotate about its own centerline 428 (FIG. 21) in directions 402, 404. However, as the bendable couplings 296 are bendable by selective pulling of wire ends 298, the centerline 428 of the end effector 100 and the centerline of the distal end of the flexible tubular members 222 can be controllably offset from each other by a single angle when one of the two bendable couplings 296 bend, or a compound double angle when both bendable couplings 296 on the end of the flexible tubular member 222 bend. Additionally, the sheath 422 and thus the flexible tubular members 222 and an illumination and camera instrument 426 therein can be advanced or retracted along direction 434 and rotated about axis 410 (FIG. 20) and thus rotate in directions 430, 432. Additionally, the flexible tubular member 222, and thus the end effector 100 attached thereto, is independently moveable in direction 436 by independent x-axis movement of the housing 256 to which it is coupled in directions 410. Herein, an operator can position the cap 436 end of the sheath 422 in a desired location in a body lumen, and then through the illuminating and camera instrument view the locations of the ends of the end effectors 100. Because each bendable coupling 296 is independently bendable in two directions orthogonal to one another, and the flexible tubular remember 22 is rotatable about axis 344, the end effector can be positioned in a multitude of orientations within the body lumen.

Referring to FIG. 22, the end of an alternative construct of the instrument 420, here instrument 440 is shown, wherein an outer sheath 442 encloses two flexible tubular members 222 (FIG. 23) and an illumination and camera instrument 446, each of which is extendable from a cantilevered cap 444 having openings 450 therein through which the tubular members 222 are selectively extendable, an opening 452 within which the lens end of a camera 454 of the illumination and camera instrument 446 is located, and a pair of illumination openings 456 within which illumination devices, for example a light emitting diode, or the end of a light guide 458, of the illumination and camera instrument 446, are located.

In contrast to cap 424 of FIG. 21, cap 444 includes an extending portion 460 extending further form the distal end 452 of the outer sheath 442 than does the portion thereof having the openings from which the end effectors 100 and bendable couplings 296 on the distal ends of the tubular members 222 are selectively extendable as shown in FIG. 23.

Figure 24:
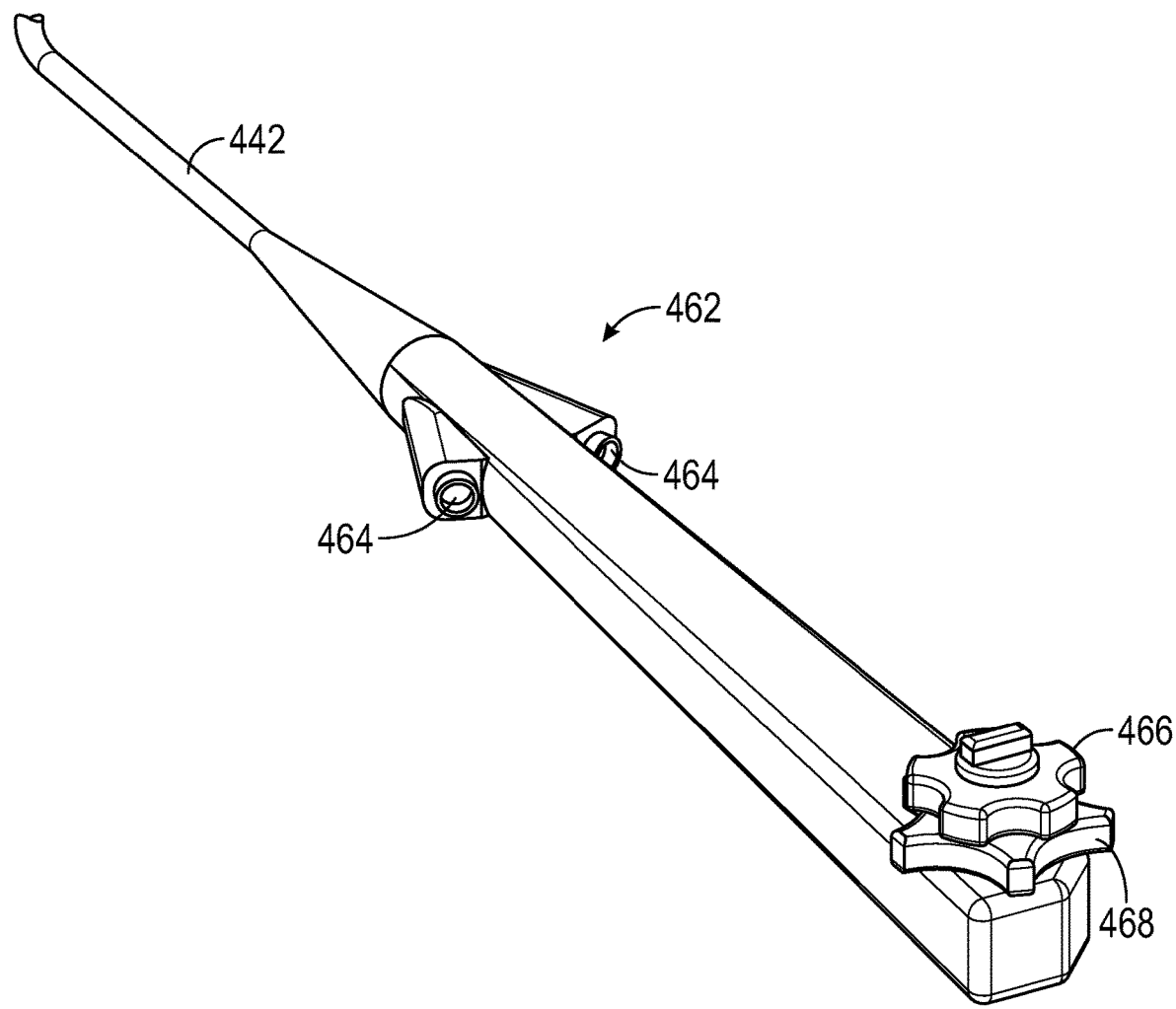
FIG. 24 is an isometric view of the control end instrument handle of the alternative instrument of FIG. 22.

FIG. 24 shows the construct of an instrument handle 462 for use with the flexible tubular members 222. Here, handle 462 includes two introduction ports 464 into which the distal ends of the flexible tubular members 222 are introduced to be extended to the distal end 452 of the outer sheath. A pair of dials 466, 468 are user controllable to move the distal end 452 of the outer sheath in 2-degrees of freedom to orient the distal end 452 of the outer sheath 442 in a desired direction.

Figure 25:
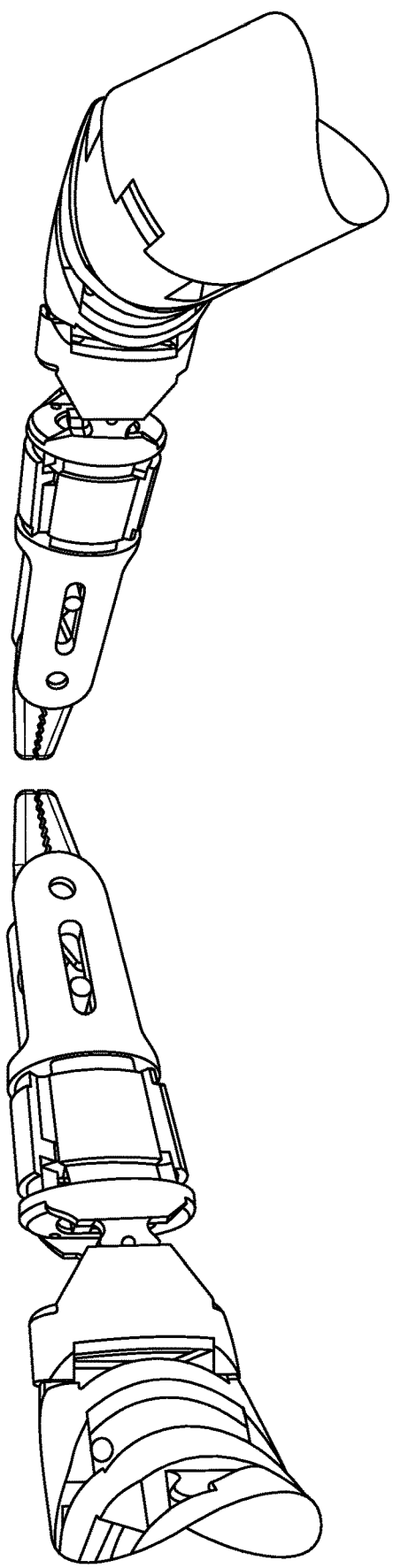
FIG. 25 is a schematic diagram of the view provided by the alternative instrument of FIG. 22.

By extending the camera forward of the location of the cap 444 from which the end effectors emerge, the camera 446 is closer to the surgical site in a patient, and a while a wide angle camera, for example having a field of view of 120 degrees, can be employed for diagnostic purposes, that same camera 446, because it lens is moved forward to the end of the extending portion 460 provides close up visualization of the surgical site and the end effectors 100 as shown in FIG. 25, to enable better viewing and control of the end effectors 100 by the surgeon or other operator thereof.

Figure 26:
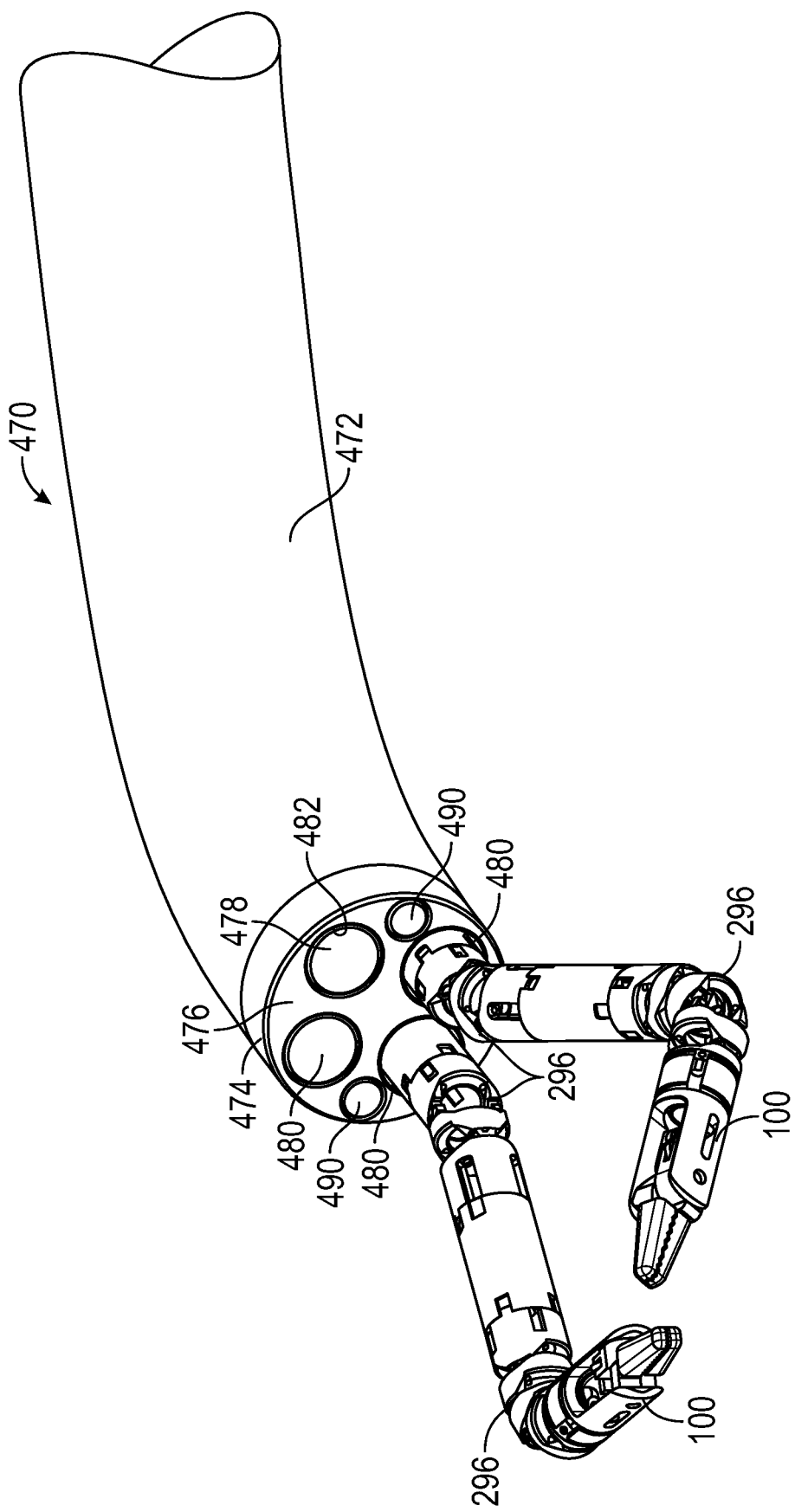
FIG. 26 is an isometric view of an additional alternative instrument construct.

Referring to FIG. 26, the end of an additional alternative construct of the instrument 420, here instrument 470 is shown, wherein an outer sheath 472 encloses two flexible tubular members and the bendable couplings 296 and end effectors 100, and an illumination and camera instrument 476. As in the prior described devices, the end effectors 100 and bendable couplings are selectively extendable through openings provided therefrom in the end cap 474. Here, in contrast to the construct of FIGS. 22 to 25 herein, the illumination and camera instrument 478 includes two cameras 480, 482, as well as two illumination elements such as light emitting diodes or light guides 490 exposed through openings are provided through the end cap 474. Here, camera 480 is a wide angle of view camera, such as on having a field of view of 120 degrees, and camera 482 has a narrower angle of view, on the order of less than 90 degrees.

Figure 27B:
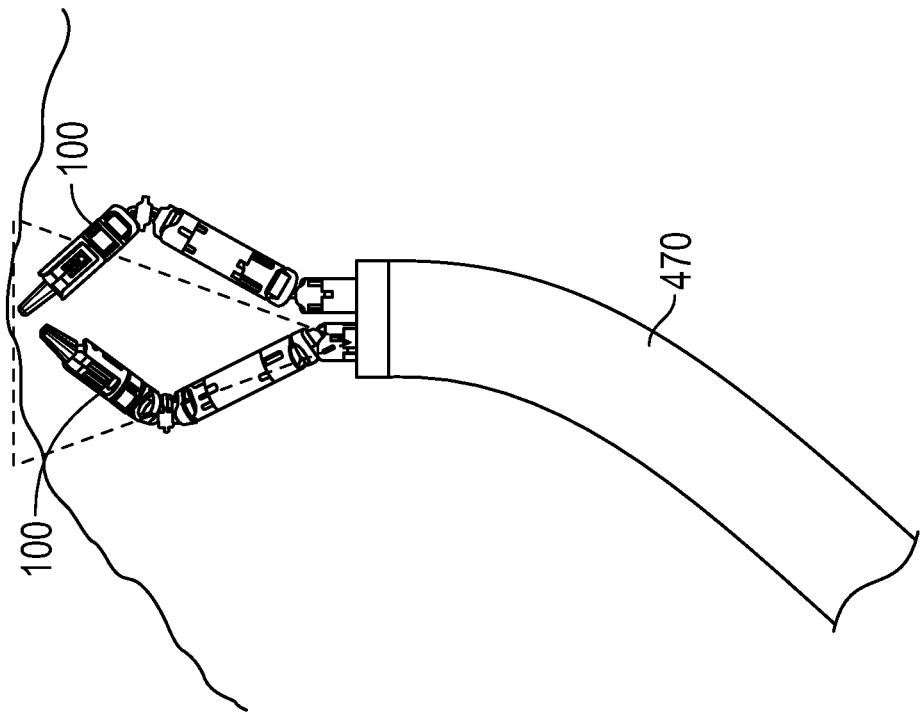
FIGS. 27a and 27b are a schematic diagram of the camera views provided by the alternative instrument of FIG. 26.
Figure 27A:
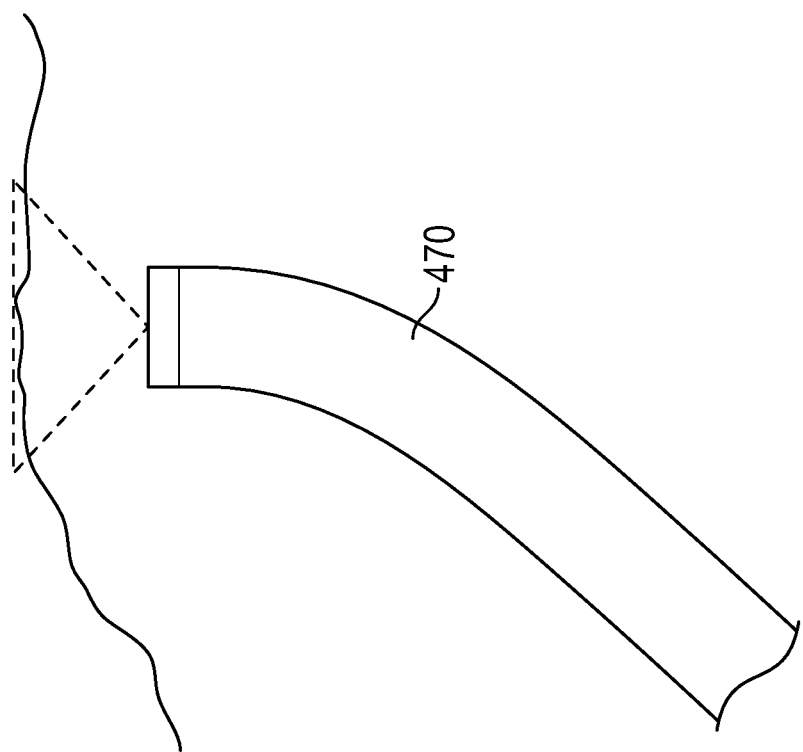

As a result, as shown in FIG. 27a, during a diagnostic use or phase of a procedure, the wide angel camera can be used to scan a body internal location, and then, as shown in FIG. 27b, the smaller angle field of view used while performing a surgical procedure at a site using the end effectors 100.

What is claimed is:

1. A mechanism to controllably move a plurality of wires within a flexible tubular member, each of the wires including a first wire end and a second wire end extending outwardly of a proximal end of the flexible tubular member, comprising:
a drive mechanism including a plurality of motors;
each of the first wire end and second wire end are individually coupled to a lead screw mechanism dedicated thereto and located in an outer housing, wherein each lead screw mechanism is configured to be dedicatedly driven by one of the motors and includes a lead screw mechanism housing, wherein each lead screw mechanism housing is fixed with respect to the outer housing;
a first lever assembly located between the drive mechanism and the first wire end and a second lever assembly located between the drive mechanism and the second wire end,
an adaptor coupling; and
a first wire actuation member at least partially disposed inwardly of a first bore extending inwardly of the adaptor coupling and moveable within the adaptor coupling in the direction toward, and away from, the first wire end, the first wire actuation member connected via the first lever assembly to the first wire end, and a second wire actuation member at least partially disposed inwardly of a second bore, different than the first bore, extending inwardly of the adaptor coupling and moveable within the adaptor coupling in the direction toward, and away from, the second wire end, the second wire actuation member connected via the second lever assembly to the second wire end, wherein movement of at least a portion of the first wire actuation member in a direction toward or away from the first wire end results in a movement in the opposite direction of the first wire end, wherein the first lever assembly is disposed in a location extended from the exterior of the adaptor coupling
wherein the first lever assembly comprises a first lever assembly first end, a first lever assembly second end, and a pivot located therebetween, and the adaptor coupling further comprises a plunger fixedly and hingedly pinned from the first lever assembly second end allowing the first lever assembly second end to swing from the plunger.

2. The mechanism of claim 1, wherein the drive mechanism is magnetically coupled to the first wire actuation member.

3. The mechanism of claim 1, the adaptor coupling further comprising at least one bore extending therethrough; and
   a bushing reciprocally moveable within the at least one bore, wherein an end of the bushing is connected to the plunger.

4. The mechanism of claim 1, wherein the first wire end is connected to the first lever assembly first end.

5. The mechanism of claim 1, wherein the adaptor coupling is positioned between the drive mechanism and the proximal end of the flexible tubular member.

6. The mechanism of claim 5, wherein the first wire actuation member comprises a plunger extending from the first lever assembly second end and the first wire end connected to the first lever assembly first end.

\* \* \* \* \*